(12) United States Patent
Zhu et al.

(10) Patent No.: US 8,617,253 B2
(45) Date of Patent: *Dec. 31, 2013

(54) VASCULAR WOUND CLOSURE DEVICE AND METHOD

(75) Inventors: Yong Hua Zhu, Redlands, CA (US); Wolff M. Kirsch, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/308,922

(22) Filed: Dec. 1, 2011

(65) Prior Publication Data

US 2012/0143246 A1 Jun. 7, 2012

Related U.S. Application Data

(63) Continuation of application No. 11/544,793, filed on Oct. 5, 2006, now Pat. No. 8,088,145.

(60) Provisional application No. 60/723,723, filed on Oct. 5, 2005.

(51) Int. Cl.
*A61F 2/02* (2006.01)

(52) U.S. Cl.
USPC ........................................... 623/23.72

(58) Field of Classification Search
None
See application file for complete search history.

(56) References Cited

U.S. PATENT DOCUMENTS

| | | |
|---|---|---|
| 3,653,388 A | 4/1972 | Tenckhoff |
| 3,677,244 A | 7/1972 | Hassinger |
| 4,060,080 A | 11/1977 | Akiyama |
| 4,166,469 A | 9/1979 | Littleford |
| 4,306,562 A | 12/1981 | Osborne |
| 4,451,256 A | 5/1984 | Weikl et al. |
| 4,532,134 A | 7/1985 | Malette et al. |
| 4,622,970 A | 11/1986 | Wozniak |
| 4,651,725 A | 3/1987 | Kifune et al. |
| 4,738,658 A | 4/1988 | Magro et al. |
| 4,744,363 A | 5/1988 | Hasson |

(Continued)

FOREIGN PATENT DOCUMENTS

| | | |
|---|---|---|
| CA | 2334226 | 4/2005 |
| CA | 2274066 | 2/2006 |

(Continued)

OTHER PUBLICATIONS

Angio-Seal, Homeostasis Puncture Closure Device Brochure, Sherwood Medical Co., Jun. 11, 1997.

(Continued)

*Primary Examiner* — Corrine M McDermott
*Assistant Examiner* — Son Dang
(74) *Attorney, Agent, or Firm* — Knobbe Martens Olson & Bear LLP

(57) ABSTRACT

A method and apparatus for closing a vascular wound includes an apparatus that can be threaded over a guidewire into place at or adjacent the wound. The apparatus includes a chamber that encloses a hemostatic material therein. When the apparatus is positioned adjacent the wound as desired, the hemostatic material is deployed from the chamber. A blocking member distal of the hemostatic material functions as a barrier to prevent the hemostatic material from entering the wound. Blood contacts the hemostatic material, and blood clotting preferably is facilitated by a hemostatic agent within the material. Thus, the vascular puncture wound is sealed by blood clot formation.

17 Claims, 31 Drawing Sheets

(56) References Cited

U.S. PATENT DOCUMENTS

| | | |
|---|---|---|
| 4,772,266 A | 9/1988 | Groshong |
| 4,889,112 A | 12/1989 | Schachner et al. |
| 4,890,612 A | 1/1990 | Kensey |
| 4,900,303 A | 2/1990 | Lemelson |
| 4,921,479 A | 5/1990 | Grayzel |
| 5,011,478 A | 4/1991 | Cope |
| 5,057,083 A | 10/1991 | Gellman |
| 5,125,904 A | 6/1992 | Lee |
| 5,129,882 A | 7/1992 | Weldon |
| 5,183,464 A | 2/1993 | Dubrul et al. |
| 5,192,301 A | 3/1993 | Kamiya et al. |
| 5,192,302 A | 3/1993 | Kensey et al. |
| 5,222,974 A | 6/1993 | Kensey et al. |
| 5,236,455 A | 8/1993 | Wilk et al. |
| 5,242,387 A | 9/1993 | Loughlin |
| 5,250,033 A | 10/1993 | Evans et al. |
| 5,259,835 A | 11/1993 | Clark et al. |
| 5,282,827 A | 2/1994 | Kensey et al. |
| 5,290,310 A | 3/1994 | Makower et al. |
| 5,292,332 A | 3/1994 | Lee |
| 5,306,254 A | 4/1994 | Nash et al. |
| 5,312,355 A | 5/1994 | Lee |
| 5,320,639 A | 6/1994 | Rudnick |
| 5,324,306 A | 6/1994 | Makower et al. |
| 5,342,393 A | 8/1994 | Stack |
| 5,350,399 A | 9/1994 | Erlebacher et al. |
| 5,370,660 A | 12/1994 | Weinstein et al. |
| 5,383,896 A | 1/1995 | Gershony et al. |
| 5,383,899 A | 1/1995 | Hammerslag |
| 5,391,183 A | 2/1995 | Janzen et al. |
| 5,397,311 A | 3/1995 | Walker et al. |
| 5,405,360 A | 4/1995 | Tovey |
| 5,411,520 A | 5/1995 | Nash et al. |
| 5,419,765 A | 5/1995 | Weldon et al. |
| 5,431,639 A | 7/1995 | Shaw |
| 5,437,631 A | 8/1995 | Janzen |
| 5,460,621 A | 10/1995 | Gertzman et al. |
| 5,486,195 A | 1/1996 | Myers et al. |
| 5,529,577 A | 6/1996 | Hammerslag |
| 5,531,759 A | 7/1996 | Kensey et al. |
| 5,545,178 A | 8/1996 | Kensey et al. |
| 5,620,461 A | 4/1997 | Muijs Van De Moer et al. |
| 5,626,601 A | 5/1997 | Gershony et al. |
| 5,643,318 A | 7/1997 | Tsukernik et al. |
| 5,645,566 A | 7/1997 | Brenneman et al. |
| 5,649,959 A | 7/1997 | Hannam et al. |
| 5,653,730 A | 8/1997 | Hammerslag |
| 5,658,298 A | 8/1997 | Vincent et al. |
| 5,662,681 A | 9/1997 | Nash et al. |
| 5,665,106 A | 9/1997 | Hammerslag |
| 5,665,107 A | 9/1997 | Hammerslag |
| 5,676,689 A | 10/1997 | Kensey et al. |
| 5,728,114 A | 3/1998 | Evans |
| 5,728,132 A | 3/1998 | Van Tassel et al. |
| 5,755,693 A | 5/1998 | Walker et al. |
| 5,759,194 A | 6/1998 | Hammerslag |
| 5,776,096 A | 7/1998 | Fields |
| 5,810,810 A | 9/1998 | Tay et al. |
| 5,836,970 A | 11/1998 | Pandit |
| 5,843,124 A | 12/1998 | Hammerslag |
| 5,906,631 A | 5/1999 | Imran |
| 5,910,155 A | 6/1999 | Ratcliff et al. |
| 5,928,266 A | 7/1999 | Kontos |
| 6,004,341 A | 12/1999 | Zhu et al. |
| 6,007,563 A | 12/1999 | Nash et al. |
| 6,048,358 A | 4/2000 | Barak |
| 6,056,768 A | 5/2000 | Cates et al. |
| 6,060,461 A | 5/2000 | Drake |
| 6,110,184 A | 8/2000 | Weadock |
| 6,155,265 A | 12/2000 | Hammerslag et al. |
| 6,197,042 B1 | 3/2001 | Ginn et al. |
| 6,287,322 B1 | 9/2001 | Zhu et al. |
| 6,287,323 B1 | 9/2001 | Hammerslag |
| 6,325,789 B1 | 12/2001 | Janzen et al. |
| 6,371,974 B1 | 4/2002 | Brenneman |
| 6,425,901 B1 | 7/2002 | Zhu et al. |
| 6,461,364 B1 | 10/2002 | Ginn et al. |
| 6,508,828 B1 | 1/2003 | Akerfeldt et al. |
| 6,524,326 B1 | 2/2003 | Zhu et al. |
| 6,589,269 B2 | 7/2003 | Zhu et al. |
| 6,613,070 B2 | 9/2003 | Redmond et al. |
| 6,632,238 B2 | 10/2003 | Ginn et al. |
| 6,649,162 B1 | 11/2003 | Biering et al. |
| 6,808,509 B1 | 10/2004 | Davey |
| 6,890,342 B2 | 5/2005 | Zhu et al. |
| 6,964,675 B2 | 11/2005 | Zhu et al. |
| 7,066,934 B2 | 6/2006 | Kirsch |
| 7,201,725 B1 | 4/2007 | Cragg et al. |
| 7,331,981 B2 | 2/2008 | Cates et al. |
| 7,780,699 B2 | 8/2010 | Zhu et al. |
| 7,931,628 B2 | 4/2011 | Zhu et al. |
| 8,012,167 B2 | 9/2011 | Zhu et al. |
| 8,088,145 B2 | 1/2012 | Zhu et al. |
| 1,064,307 A1 | 6/2013 | Fleming |
| 2001/0004710 A1 | 6/2001 | Felt et al. |
| 2001/0018598 A1 | 8/2001 | Cruise et al. |
| 2001/0053922 A1 | 12/2001 | Zhu et al. |
| 2002/0022822 A1 | 2/2002 | Cragg et al. |
| 2002/0072767 A1 | 6/2002 | Zhu |
| 2002/0072768 A1 | 6/2002 | Ginn |
| 2002/0077656 A1 | 6/2002 | Ginn et al. |
| 2002/0077657 A1 | 6/2002 | Ginn et al. |
| 2002/0147479 A1 | 10/2002 | Aldrich |
| 2003/0023267 A1 | 1/2003 | Ginn |
| 2003/0044380 A1 | 3/2003 | Zhu et al. |
| 2003/0045893 A1 | 3/2003 | Ginn |
| 2003/0109820 A1 | 6/2003 | Gross et al. |
| 2003/0125264 A1 | 7/2003 | Malik |
| 2003/0158578 A1 | 8/2003 | Pantages et al. |
| 2004/0054346 A1* | 3/2004 | Zhu et al. ............ 604/507 |
| 2004/0059348 A1 | 3/2004 | Geske et al. |
| 2005/0085856 A1 | 4/2005 | Ginn |
| 2005/0095275 A1 | 5/2005 | Zhu et al. |
| 2005/0107826 A1* | 5/2005 | Zhu et al. ............ 606/213 |
| 2005/0118238 A1 | 6/2005 | Zhu et al. |
| 2005/0123588 A1 | 6/2005 | Zhu et al. |
| 2005/0142172 A1 | 6/2005 | Kirsch et al. |
| 2005/0155608 A1 | 7/2005 | Pavcnik |
| 2005/0209637 A1 | 9/2005 | Zhu et al. |
| 2005/0240137 A1 | 10/2005 | Zhu et al. |
| 2006/0064124 A1 | 3/2006 | Zhu et al. |
| 2006/0100664 A1 | 5/2006 | Pai et al. |
| 2010/0211000 A1* | 8/2010 | Killion et al. ............ 604/57 |

FOREIGN PATENT DOCUMENTS

| | | |
|---|---|---|
| EP | 0 646 350 A1 | 4/1995 |
| EP | 0 493 810 B1 | 11/1995 |
| EP | 0 745 350 A1 | 12/1995 |
| EP | 0 955 900 B1 | 7/1997 |
| EP | 0 788 769 A1 | 8/1997 |
| EP | 0 818 178 B1 | 1/2001 |
| JP | H6-339483 | 12/1994 |
| JP | H10-43311 | 2/1998 |
| JP | 2005-230427 | 9/2005 |
| WO | WO 94-21306 A1 | 9/1994 |
| WO | WO 95-05206 A2 | 2/1995 |
| WO | WO 96 10374 A1 | 4/1996 |
| WO | WO 96 24291 A1 | 8/1996 |
| WO | WO 97 20505 A1 | 6/1997 |
| WO | WO 98-24374 A1 | 6/1998 |
| WO | WO 99-20326 | 4/1999 |
| WO | WO 99 22646 A1 | 5/1999 |
| WO | WO 99-62405 A1 | 12/1999 |
| WO | WO 00-02488 A1 | 1/2000 |
| WO | WO 00-07640 A2 | 2/2000 |
| WO | WO 00-19912 A1 | 4/2000 |
| WO | WO 00-33744 A1 | 6/2000 |
| WO | WO 01-62159 A2 | 8/2001 |
| WO | WO 02-05865 A2 | 1/2002 |
| WO | WO 02-09591 A2 | 2/2002 |

(56) References Cited

FOREIGN PATENT DOCUMENTS

| WO | WO 03-008002 A1 | 1/2003 |
| WO | WO 03-008003 A1 | 1/2003 |
| WO | WO 03-105697 A1 | 12/2003 |
| WO | WO 2004/110284 A1 | 12/2004 |
| WO | WO 2005/016152 A2 | 2/2005 |
| WO | WO 2007/044510 | 4/2007 |

OTHER PUBLICATIONS

Gershony, Gary, M.D., A Novel Femoral Access Site Closure Device: Duet, Early European Clinical Trials, Los Angeles Cardiology Associates, Seminar, Coronary Interventions, Oct. 16-18, 1997.

"Microporous Polysaccharide Hemospheres Provides Effective Topical Hemostasis in a Human Modified Bleeding Time Incision Model" by MEDAFORE, Sep. 2002.

* cited by examiner

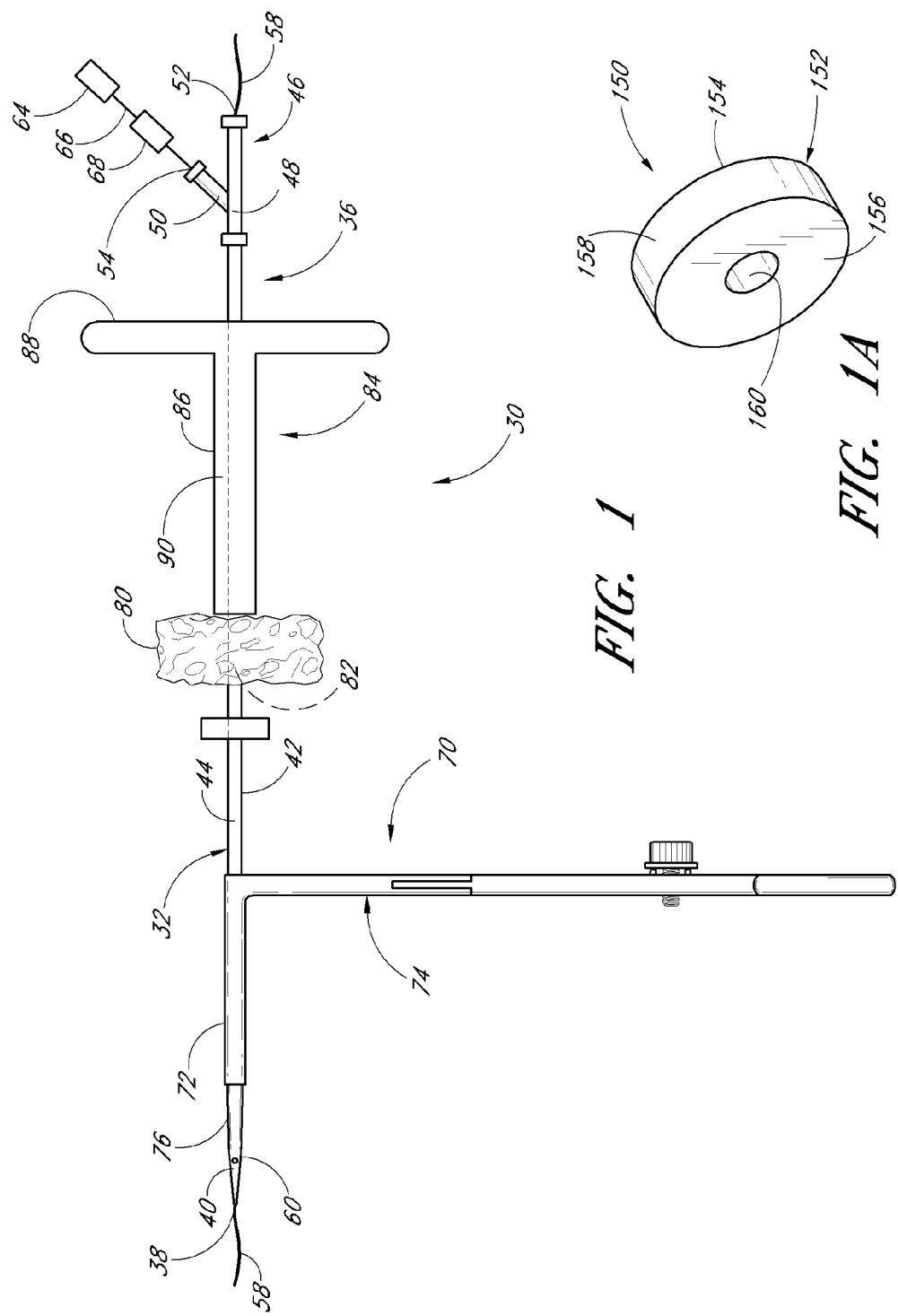

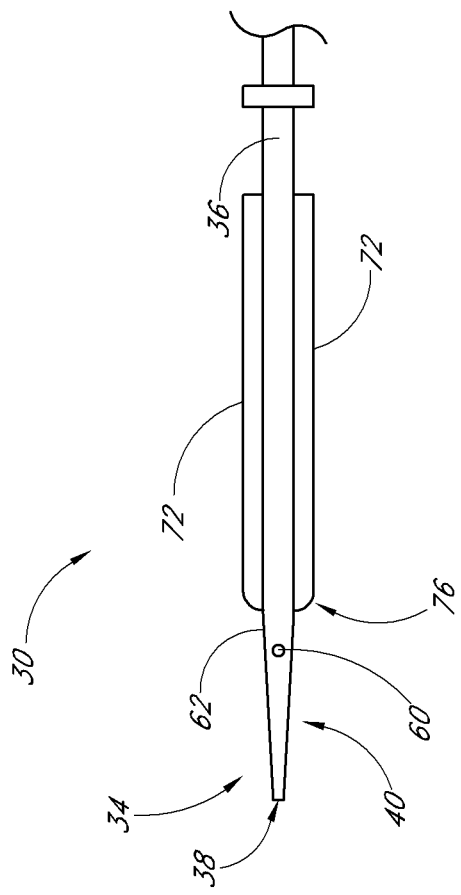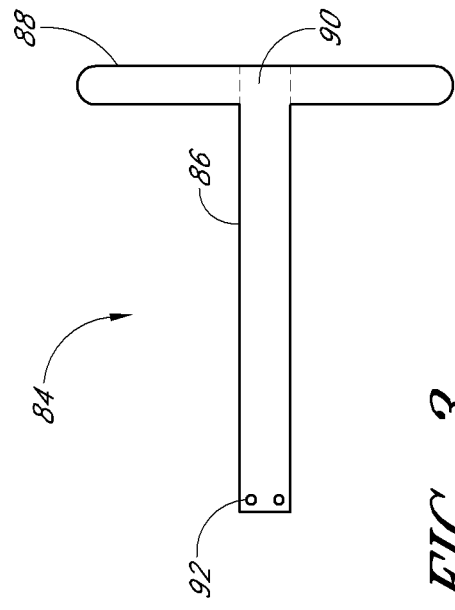

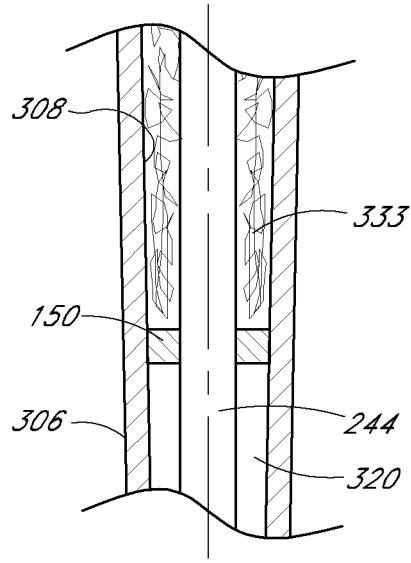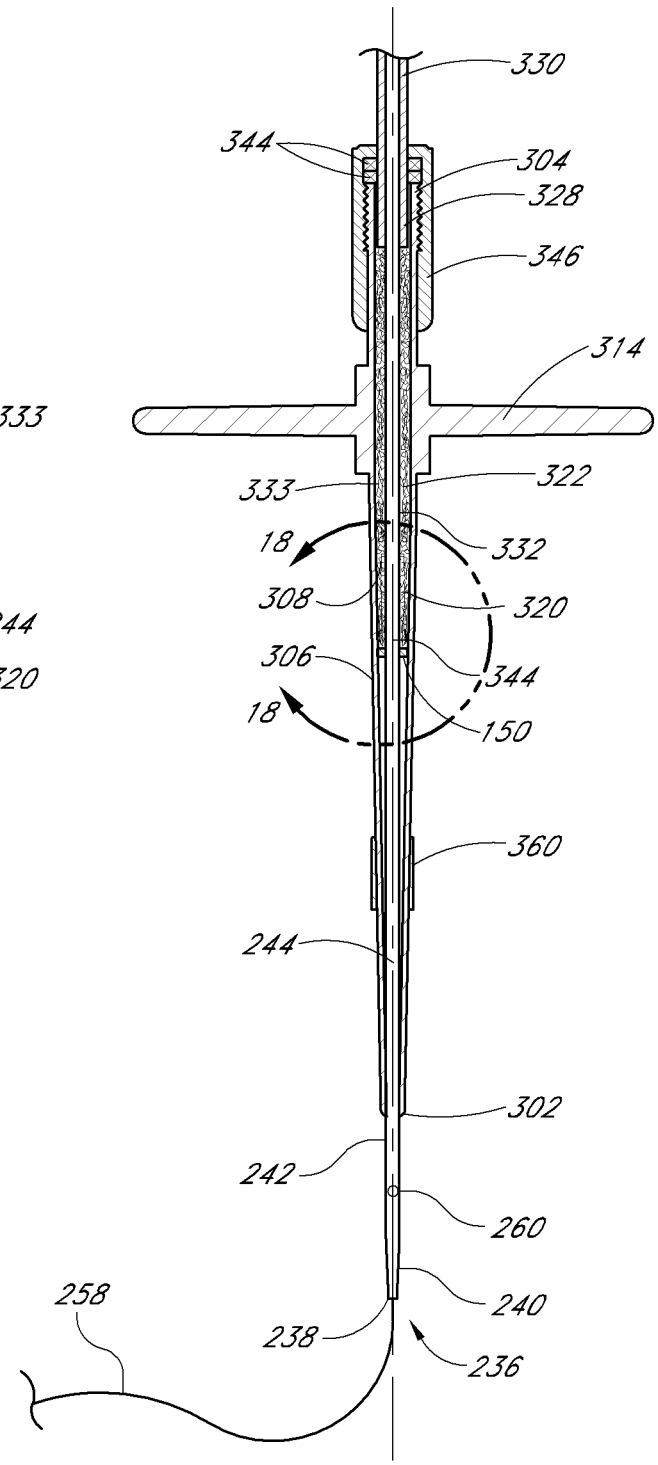
FIG. 18
FIG. 17A

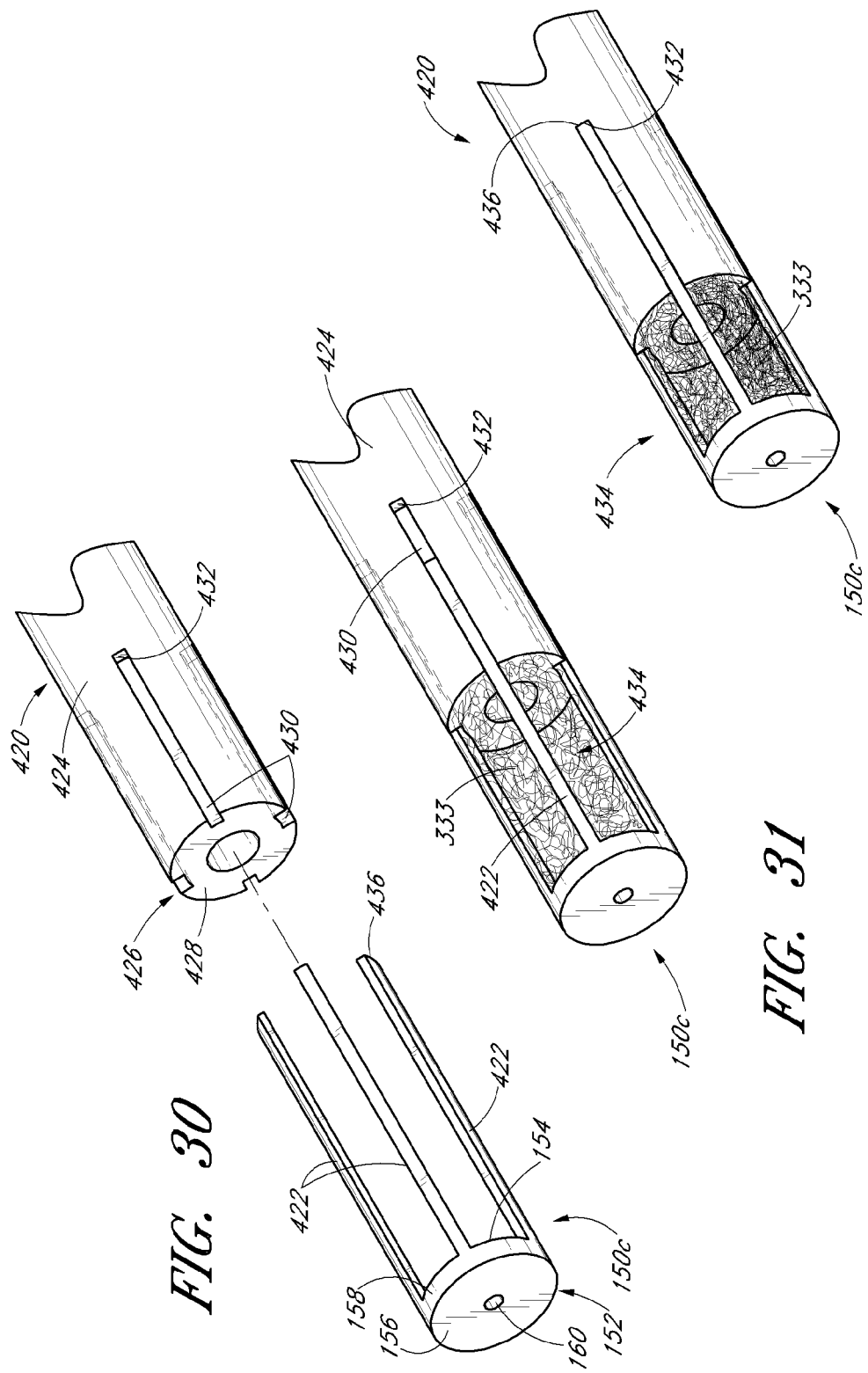

VASCULAR WOUND CLOSURE DEVICE AND METHOD

RELATED APPLICATIONS

This application is a continuation of U.S. application Ser. No. 11/544,793, filed Oct. 5, 2006, now U.S. Pat. No. 8,088,145 which claims the benefit of U.S. Provisional Application Ser. No. 60/723,723, which was filed Oct. 5, 2005, the entirety of which is hereby incorporated by reference.

BACKGROUND OF THE INVENTION

1. Field of the Invention

The present invention generally relates to a system that facilitates closure of openings in blood vessels. More specifically, the present invention delivers a material adjacent a vessel.

2. Description of the Related Art

In many medical procedures, it is necessary to locate an opening in tissue so that some form of treatment, diagnosis or revision, can be applied to that opening. For example, in order to perform transluminal balloon angioplasty, an opening is created in an artery in order to insert a catheter for delivering a balloon within the blood vessel. This opening must later be closed.

Transluminal balloon angioplasty is used in the treatment of peripheral vascular disease to increase or restore blood flow through a significantly narrowed artery in a limb; it is also used in the treatment of blockage of the coronary arteries. In fact, coronary angioplasty has emerged as a major viable alternative to bypass surgery for revascularization of stenotic and occluded coronary arteries. Unlike bypass surgery, angioplasty does not require general anesthesia, opening of the chest wall, use of a heart-lung machine, or transfusion of blood. Angioplasty is not only less invasive and less traumatic to the patient, but is also less expensive because of the shorter hospital stay and shorter recovery time.

Transluminal balloon angioplasty is performed by first inserting a hollow needle through the skin and surrounding tissues and into the patient's femoral artery. A guidewire is advanced through the hollow needle and into the artery, then along the patient's vasculature toward the site of the blocked blood vessel or valve to be treated. Radiographic imaging is used to help guide the guidewire through the vascular system and into position adjacent the stenosis to be treated. A balloon catheter is then threaded over the guidewire and advanced until the deflated balloon is within the stenosis. The balloon is then repeatedly inflated to widen the narrowed blood vessel. After the procedure is complete, the catheter and guidewire are withdrawn from the blood vessels and the patient.

After the catheter used during angioplasty is removed, the puncture wound in the femoral artery must be closed and the bleeding through the puncture site in the artery stopped. Often, ice packs and/or pressure are applied to the area surrounding the wound for a period lasting up to several hours in an attempt to stop the bleeding. There exists, however, a significant chance that the wound will reopen and begin bleeding again when the patient moves. Another possible complication is the development of a false aneurysm, which increases the risks of both infection and reopening.

Efforts have been made to close the puncture wound using staples, clips, collagen plugs, and sutures. These efforts, and the devices incident thereto, tend to be cumbersome and complicated and involve significant potential for dangerous complications. For example, if foreign matter, such as collagen, intrudes into the blood vessel, it could prompt blood clotting, leading to undesirable consequences.

Various other treatments and diagnostic procedures involve catheters advanced through a blood vessel. Such procedures necessitate closure of the access hole into the vessel. Further, other wounds in the vasculature of a patient can also be difficult to locate, access and close. Thus, a device and method to facilitate locating and closing such wounds in the vasculature of a patient would be beneficial. A device having the ability to consistently and reliably locate, isolate and close the puncture wound would eliminate the prolonged bleeding currently associated with such wounds.

SUMMARY OF THE INVENTION

Accordingly, there is a need in the art for a device and method for precisely locating a blood vessel wound and sealing the wound.

In accordance with one embodiment, the present invention provides a vascular wound closure device. The device comprises an elongate guide sized and configured to extend partially through a vascular puncture; and a multi-layer closure portion disposed circumferentially about the elongate guide. The closure portion is movable distally over the catheter. A first member of the closure portion is configured to engage a blood vessel wall, and has an outer diameter that is greater than a diameter of the vascular puncture. A second member of the closure portion comprises a hemostatic material. At least part of the first member is arranged distal of the second member. The first member engages an outer surface of the elongate guide so that the hemostatic material of the second member is prevented from moving distally between the first member and the guide.

In another embodiment, the device additionally comprises a push member adapted to urge the closure portion distally over the elongate guide. In yet another embodiment, the first member is movable separately from the second member. In a further embodiment, the second member is adhered to the first member. In another embodiment, the guide comprises a catheter. Yet another embodiment additionally comprises a retractor disposed about the catheter distal of the first member. In still another embodiment, the guide comprises a guidewire.

In a still further embodiment, the push member is arranged about the guide, and the push member is adapted to engage the first member so that a space is defined between a distal surface of the push member and a proximal surface of the first member.

In yet another embodiment, the first member comprises an aperture adapted to slidably accommodate the guide. The aperture is biased to generally close when the guide is removed therefrom.

Another embodiment additionally comprises a delivery chamber. The first member and second member are disposed at least partially within the delivery chamber. In a still further embodiment, the first member comprises a hemostatic material. In still another embodiment, the first member is generally flexible. But in another embodiment, the first member is generally rigid. In one embodiment, the first member comprises an elastic member, and in another embodiment, the first member comprises a mesh. In some embodiments, the first member is hydrophilic. A further embodiment comprises a first member comprising chitosan. In another embodiment, the second member comprises a fibrous chitosan fleece. In still another embodiment, the first member has a greater density than the second member.

In accordance with another embodiment, the present invention provides a medical method. The method comprises puncturing a blood vessel; inserting one or more therapy implements through the puncture wound and into the blood vessel; performing a therapeutic surgical procedure via the one or more therapy implements; inserting a closure catheter at least partially into the puncture wound; and providing a blocking member disposed about the outer surface of the closure catheter. The blocking member has an outer diameter greater than the puncture wound. The method further comprises advancing the blocking member over an outer surface of the closure catheter and into engagement with the blood vessel outer wall; and advancing a hemostasis-promoting material over the closure catheter.

In accordance with one embodiment, the therapeutic surgical procedure performed via the one or more therapy implement comprises a transluminal balloon angioplasty procedure.

In another embodiment, the blocking member has greater structural rigidity than the hemostatic material. In yet another embodiment, the closure catheter has an outer diameter greater than a greatest diameter of the one or more therapy implements that were inserted through the puncture. In still another embodiment, the blocking member has an outer diameter greater than an outer diameter of the closure catheter.

For purposes of summarizing the preferred embodiments and the advantages achieved over the prior art, certain embodiments and advantages have been described herein above. Of course, it is to be understood that not necessarily all such advantages may be achieved in accordance with any particular embodiment. Thus, for example, those skilled in the art will recognize that the invention may be embodied or carried out in a manner that achieves or optimizes one advantage or group of advantages as taught herein without necessarily achieving other objects or advantages as may be taught or suggested herein.

The embodiments discussed above and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 1 is a side view of an embodiment of a vascular closure apparatus shown assembled and ready for use.

FIG. 1A is a perspective view of a blocking member employed in accordance with the apparatus of FIG. 1.

FIG. 2 is a back view of a distal portion of the apparatus of FIG. 1.

FIG. 3 is a side view of a push member in accordance with one embodiment.

FIG. 17A is a close up view of a portion of the apparatus of FIG. 12.

FIG. 18 is a close up view taken along lines 18-18 of FIG. 17A.

FIG. 30 shows a perspective view of another embodiment of a blocking member adapted to releasably engage a distal end of a complementarily formed pusher member.

FIG. 31 shows the arrangement of FIG. 30 partially engaged and with a hemostatic material disposed in a space between the blocking member and pusher member.

FIG. 32 shows the arrangement of FIG. 31 with the blocking member engaging the pusher member in a manner so that the space cannot be further compressed.

DETAILED DESCRIPTION OF PREFERRED EMBODIMENTS

Figure 4:
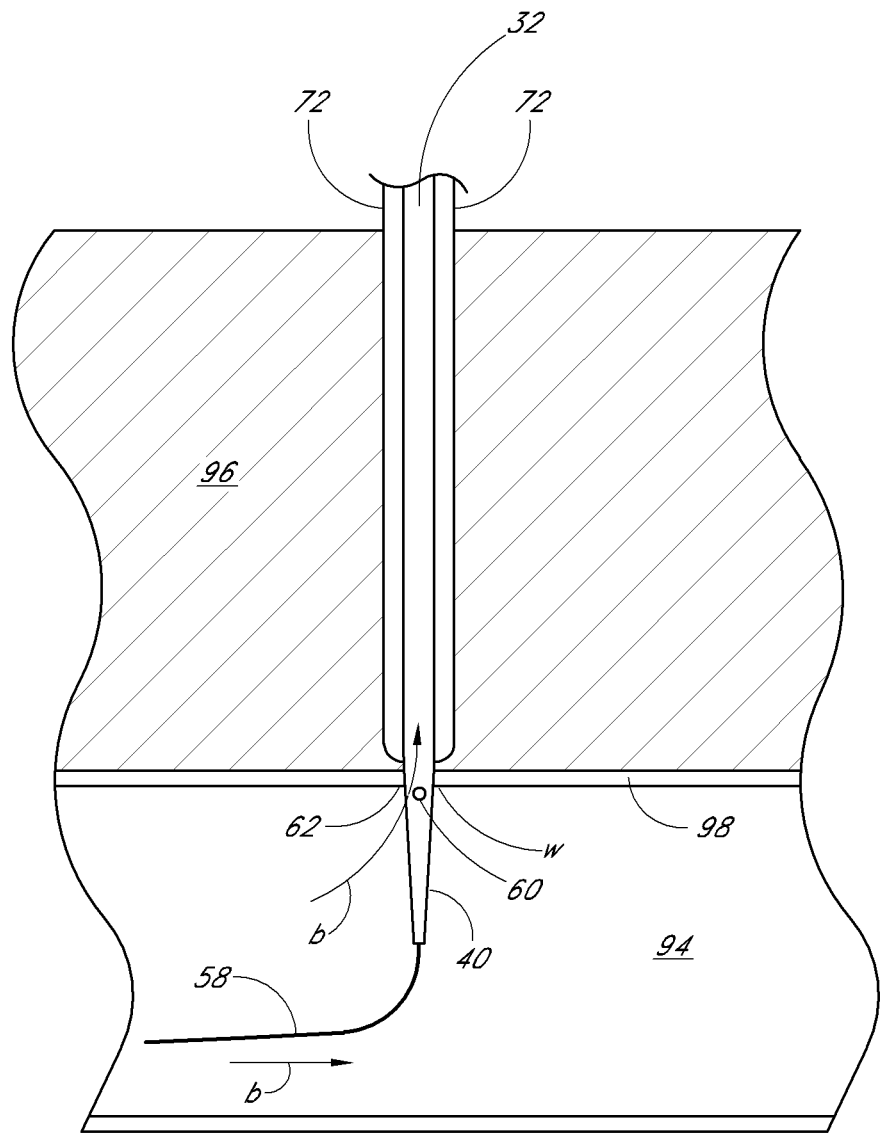
FIG. 4 shows the apparatus of FIG. 1 advanced over a guidewire into a blood vessel of a patient.

The present embodiments are especially useful for closing vascular puncture wounds that are difficult to access and/or visualize. It is difficult to directly and accurately modify a wound in a blood vessel in order to close such wounds. Additionally, there are pitfalls associated with directly modifying the blood vessel. For example, since the clinician cannot see the wound, it is difficult to correctly place closure media such as sutures, staples, or clips. Incorrect placement of such closure media likely results in inadequate closure; the puncture wound remains open, perhaps without the clinician being aware. Additionally, incorrect placement of closure media may cause permanent damage to the vessel, including tearing and additional puncture wounds. Further, if closure media extends through the wound and into the blood flow, this media can increase the likelihood of thrombus formation or could introduce potentially toxic substances into the bloodstream. Of course, closure media inadvertently released into the bloodstream could lead to serious blood vessel blockage complications.

With reference to FIG. 1, an embodiment of a vascular wound closure assembly 30 includes an elongate catheter 32 having a distal end 34 and a proximal end 36. A distal opening 38 is formed through the distal end 34 of the catheter 32 and opens along a longitudinal axis of the catheter 32. The catheter 32 preferably includes a tapered tip 40 at the distal end 34. An elongate main body 42 of the catheter 32 is disposed proximal the tapered tip 40. Preferably the main body 42 has a substantially uniform diameter along its length. A lumen 44 extends longitudinally within the catheter 32 from the distal opening 38 to the proximal end 36.

In the illustrated embodiment, a connector portion 46 is provided on the proximal end 36 of the catheter 32. The connector portion 46 includes a main lumen 48 and a secondary lumen 50. The main lumen 48 extends along the longitudinal axis of the catheter 32 and is coextensive with the catheter lumen 44. The secondary lumen 50 extends outwardly from the main lumen 48, but communicates with the main lumen 48 and the catheter lumen 44. Preferably, the main and secondary lumens 48, 50 are disposed generally in a "Y" shape. A proximal opening 52 is provided at the proximal end of the main lumen 48 and, like the distal opening 38, opens along the longitudinal axis. A secondary opening 54 is provided at the proximal end of the secondary lumen 50.

The distal and proximal openings 38, 52 preferably are sized and adapted to accommodate a guidewire 58 such as a guidewire used in angioplasty and other vascular procedures. As such, the guidewire 58 can be threaded through the catheter 32 and the catheter can be advanced over the guidewire 58.

At least one hole 60 is formed through a side wall of the catheter 32 near the distal end 34 of the catheter 32. Preferably, at least two holes 60 are provided. All of the holes 60 preferably are disposed substantially the same distance from the distal end 34 of the catheter 32.

With continued reference to FIG. 1, a vacuum or other source of suction 64 is selectively provided and communicates, through tubing 66, with the secondary lumen 50 of the catheter connector portion 46. Thus, a vacuum can be drawn through the catheter lumen 44. Preferably, the distal and proximal openings 38, 52, which accommodate the guidewire 58, are sized so that the guidewire 58 substantially plugs the openings; thus, the vacuum is drawn mostly through the holes 60. In the following embodiment, a viewing port 68 is arranged between the source of suction 64 and the catheter 32.

The viewing port 68 is configured to allow a clinician to view the material that is drawn by suction through the holes 60 and through the catheter lumen 44. The viewing port 68 will be discussed in more detail below.

With reference to FIGS. 1 and 2, a retractor 70 preferably is mounted on the catheter 32. The retractor 70 includes opposing elongate retractor arms 72 that are aligned longitudinally on the catheter 32. A retractor body 74 is configured to selectively open and close the retractor arms 72 when operated by a clinician. The elongate retractor arms 72 of the retractor 70 are positioned on the catheter 32 so that distal ends 76 of the arms are positioned proximal of the catheter holes 60 a distance that is at least the same as the width of an artery wall, preferably at least about 0.5 to 2 millimeters.

It is to be understood that the present device can include structure that is somewhat different than the particular structure shown in FIGS. 1 and 2. For example, other catheter and retractor structures can appropriately be used. For example, some acceptable catheter and retractor embodiments are presented in U.S. application Ser. No. 09/325,982, filed on Jun. 4, 1999, now U.S. Pat. No. 6,287,322 and U.S. application Ser. No. 10/919,939, which was filed on Aug. 16, 2004, each of which is hereby incorporated by reference in its entirety.

With specific reference again to FIG. 1, a hemostatic member 80 is arranged on the catheter 32 proximal of the retractor 70. As will be discussed in more detail below, the hemostatic member comprises a material that is made of or includes a hemostatic agent. The hemostatic agent is adapted to aid blood clotting. In one embodiment, the hemostatic member 80 comprises a sponge or sponge-like material. In this description, the term sponge is intended to be a broad term that is used in accordance with its ordinary meaning and refers to, without limitation, a material that is at least partially porous and is adapted to allow at least some blood to flow into and within the material so as to soak the material with blood. For example, a sponge may include a natural or artificial sponge, a woven or non-woven cloth, a puff made of fibers arranged generally randomly, or the like. Additionally, a sponge may comprise a material that soaks up at least a portion of blood that may come in contact with the material, or may comprise a material that doesn't soak up blood.

For purposes of this description, the hemostatic member 80 is referred to as the sponge 80. However, it is to be understood that use of the term "sponge" should not be taken to limit the scope of materials that can be used as the hemostatic member. In fact, any material that significantly aids or facilitates blood clotting can be used as the hemostatic member.

Throughout this description, the term hemostatic agent is used as a broad term in its ordinary sense and refers to, without limitation, an agent that significantly promotes blood clotting. Such an agent may take many forms, including liquid, powder, solid, beads, etc. and can include or be combined with a substrate or carrier. The term hemostatic material is also used in this description as a broad term used in its ordinary sense. It refers to, without limitation, any material having properties that significantly promotes blood clotting. Thus, hemostatic material can include a hemostatic agent taken alone or in combination with a substrate or carrier that is formed separately from the agent. The term hemostatic material includes hemostatic sponges.

Preferably, the sponge 80 extends circumferentially around the catheter main body 42, and is arranged so that it can be slid longitudinally along and over the catheter 32. Most preferably, the catheter 32 extends through a passageway 82 through the sponge 80. The passageway 82 preferably comprises a slit or other aperture formed through the sponge 80.

Preferably portions of the sponge 80 at or adjacent the passage 82 deform to accommodate the catheter 32.

With specific reference to FIGS. 1 and 1A, preferably a blocking member 150 is arranged on the catheter 32 distal of the sponge 80. In the illustrated embodiment, the blocking member 150 substantially surrounds the catheter 32 and is generally ring-shaped (see FIG. 1A). Preferably, the blocking member 150 comprises a generally ring-shaped body 152 having a proximal surface 154, a distal surface 156, a perimeter surface 158, and an inner aperture 160. Preferably the inner aperture 160 has an inner diameter substantially the same as the outer diameter of the catheter 32 so that there is very little, if any, space between the ring 150 and the catheter 32.

Preferably the inner aperture 160 is sized and/or treated so that the blocking member 150 is slideable over the outer surface of the catheter 32. In an additional embodiment, the aperture 160 inner diameter is slightly less than the outer diameter of the ring catheter 32. This will ensure an even better seal between the blocking member 150 and the catheter 32 so that no hemostatic material 80 can work its way distally between the blocking member 150 and the catheter 32 and further into the puncture wound w. In another embodiment, surface of the blocking member inner aperture is lubricated so as to facilitate sliding over the outer surface of the catheter 32, even if the fit between the catheter 32 and blocking member 150 is relatively tight.

A push member 84 is also arranged on the catheter 32 proximal of the sponge 80. With reference also to FIG. 3, the push member 84 comprises a body portion 86 and a proximal handle portion 88. An elongate lumen 90 is formed through the body portion 86. As shown in FIG. 1, the lumen 90 preferably encircles the catheter 32 so as to allow the push member 84 to slide relative to the catheter 32. A plurality of holes 92 preferably are formed through the body portion 86 at a point near the distal end of the push member 84.

As will be discussed in more detail below in connection with FIG. 4, the vascular wound closure assembly 30 enables a clinician to precisely locate a subcutaneous vascular wound "w", access the wound w, and deliver the hemostatic sponge 80 and blocking member to the wound site. The hemostatic sponge 80 includes a hemostatic agent that helps facilitate closure of the wound w when in place at or adjacent the wound w.

In order to properly apply the hemostatic sponge 80, the vascular closure assembly 30 first precisely locates and provides access to the vascular wound w. It is to be understood that the present method and apparatus can be used to close various vascular and other wounds. FIGS. 1-11, and the accompanying discussion, present an example using an embodiment to close a puncture wound w in a patient's femoral artery 94.

With specific reference to FIGS. 1, 2, 4 and 5, in order to precisely locate and provide access to a femoral artery puncture wound w, the catheter 32 is first threaded over a guidewire 58 that has been previously inserted into the patient's femoral artery 94 through the puncture wound w. The lumen 44 is attached to the source of suction 64 and the assembly 30 is advanced over the guidewire 58 through a patient's tissue 96 so that the distal tip 40 of the catheter 32 extends through the vascular puncture wound w.

As the assembly 30 is advanced, the source of suction 64 draws bodily fluids through the holes 60. The fluids pass through the viewing port 68, which allows the clinician to identify the fluids being withdrawn. The viewing port 68 can have any suitable structure or location. For example, the viewing port can comprise clear tubing attached to the catheter, a substantially transparent syringe that functions as both a source of suction and a viewing port, or a portion of the catheter that is substantially transparent. Most preferably, the catheter 32 is formed of a transparent material so that the clinician becomes aware as soon as blood begins to be drawn through the catheter.

Figure 5:
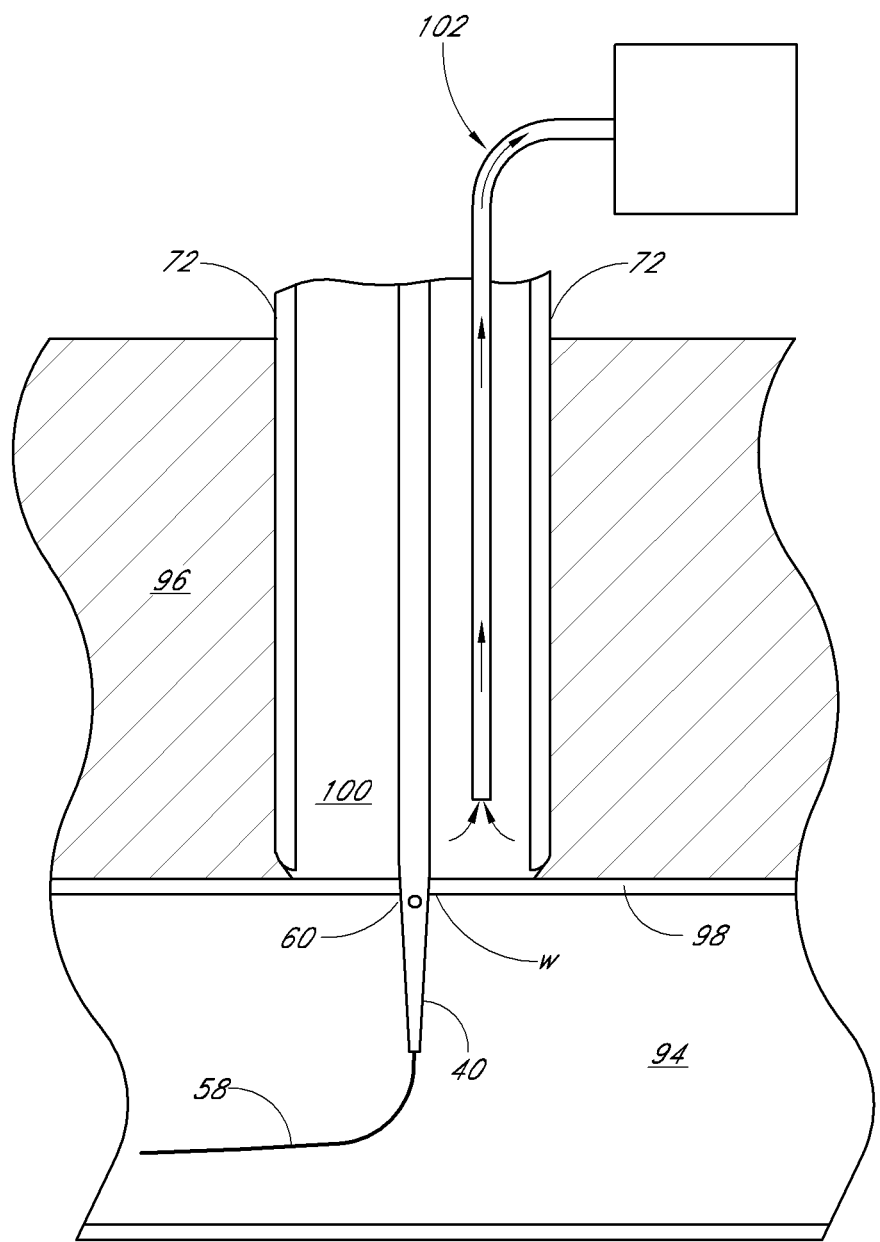
FIG. 5 shows the arrangement of FIG. 4 with the retractor arms open and a suction tool in use.

When the holes 60 pass the artery wall 98 and enter the blood vessel 94, as shown in FIG. 4, blood "b" begins to be drawn through the holes 60 into the catheter 32 and is conducted past the viewing port 68. Thus, when blood b is observed in the viewing port 68, the clinician will know that the holes 60 have just passed into the puncture wound w and that the distal ends 76 of the retractor arms 72 are thus positioned at or near the outer wall 98 of the artery 94, preferably within about 3 mm of the artery wall 98, and more preferably within about 2 mm of the artery wall 98. The retractor arms 72 are then separated as shown in FIG. 5, thus drawing surrounding tissue 96 away from the wound w and creating a field 100 around the puncture wound w. Separating the retractor arms 72 also creates an access path to the wound w. The catheter 32 remains disposed partially within the puncture wound w, preferably effectively plugging the wound and preferably substantially preventing blood from flowing through the wound. Preferably, the portion of the catheter 32 proximal of the holes 60 flexes the edges of the wound w to enhance the seal between the catheter 32 and the puncture wound edges.

In another embodiment, a portion of the catheter 32 at/or proximal the holes 60 has a larger diameter than other parts of the catheter 32. Such a larger-diameter portion even more effectively plugs the wound w.

With continued reference to FIG. 5, in one embodiment a suction tool 102 and/or irrigation tool can be used to clear away bodily fluids and other matter that may be within the field 100 and to clean the wall 98 of the blood vessel 94 adjacent the puncture wound w. In other embodiments, such cleaning of the field 100 is not performed.

Figure 6:
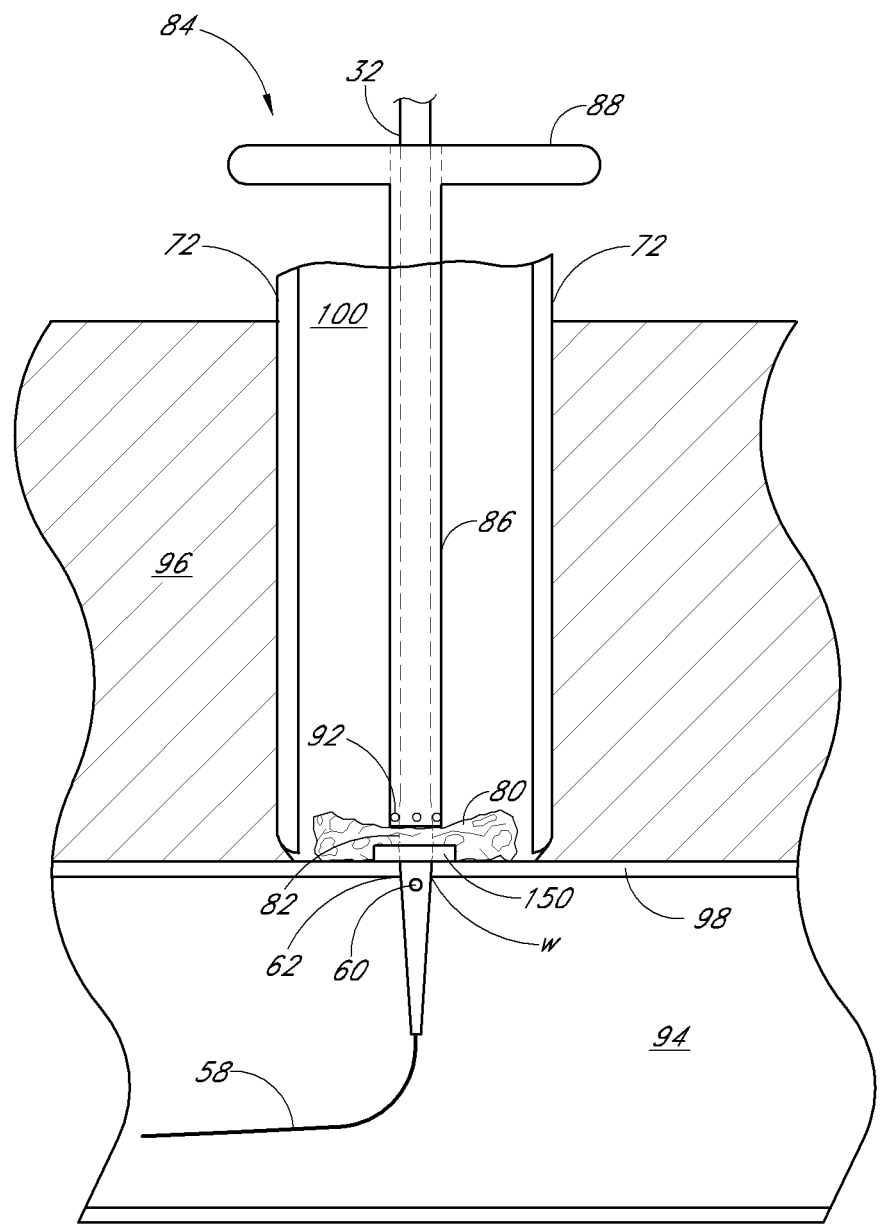
FIG. 6 shows the arrangement of FIG. 5, wherein a hemostatic sponge has been advanced into contact with the blood vessel wall.

With reference next to FIG. 6, once the puncture wound w has been precisely located, the push member 84 is advanced distally along the catheter 32, thus advancing the sponge 80 and blocking member into contact with the vessel wall 98 so as to surround the puncture wound w. As mentioned above and discussed in more detail below, the sponge 80 comprises a hemostatic agent that will help accelerate blood clot formation at the wound site w in order to help the wound heal faster. In a preferred embodiment, the blocking member also comprises a hemostatic agent.

In the illustrated embodiment, the distal end of the pusher member 84 only directly contacts a portion of the proximal end of the sponge 80. However, preferably, the sponge 80 is sufficiently cohesive that advancement of the pusher member 84 moves the entire sponge 80 distally.

In the illustrated embodiment, the blocking member 150 comprises a hydrophilic hemostatic material such as a fibrous non-woven chitosan fabric. Although the preferred blocking member is made of a fibrous material, as are some embodiments of sponge 80, in this embodiment the blocking member 150 preferably is processed so as to have a greater density, and thus greater rigidity, than the sponge. As such, the blocking member 150 is structurally sound enough to withstand pressures exerted via the push member 84 without substantially deforming to the degree that gaps will be formed between the blocking member 150 and the catheter 32 and/or between the blocking member 150 and the blood vessel 94. As such, during use, there are no gaps that would allow fibers or other portions of the sponge 80 to work their way past the blocking member 150 and into the wound w. Additionally, since in the illustrated embodiment the blocking member is relatively rigid and preferably has an outer diameter greater than the diameter of the wound w, the blocking member 150 itself will not pass through the wound and into the blood vessel 94.

Notwithstanding the positioning of the blocking member 150 between the hemostatic sponge 80 and the puncture wound w, blood escaping from the puncture w will still flow to the hemostatic sponge 80, which promotes clotting so as to close the wound.

The sponge 80 preferably is mounted onto the catheter 32 so as to substantially encircle the catheter 32. Thus, since the tip 40 of the catheter is disposed in the wound, and since the blocking member 150 substantially immediately surrounds the wound w, the sponge 80 substantially surrounds the blocking member 150, and preferably a portion of the sponge 80 is positioned adjacent the vessel wall 98.

Figure 7:
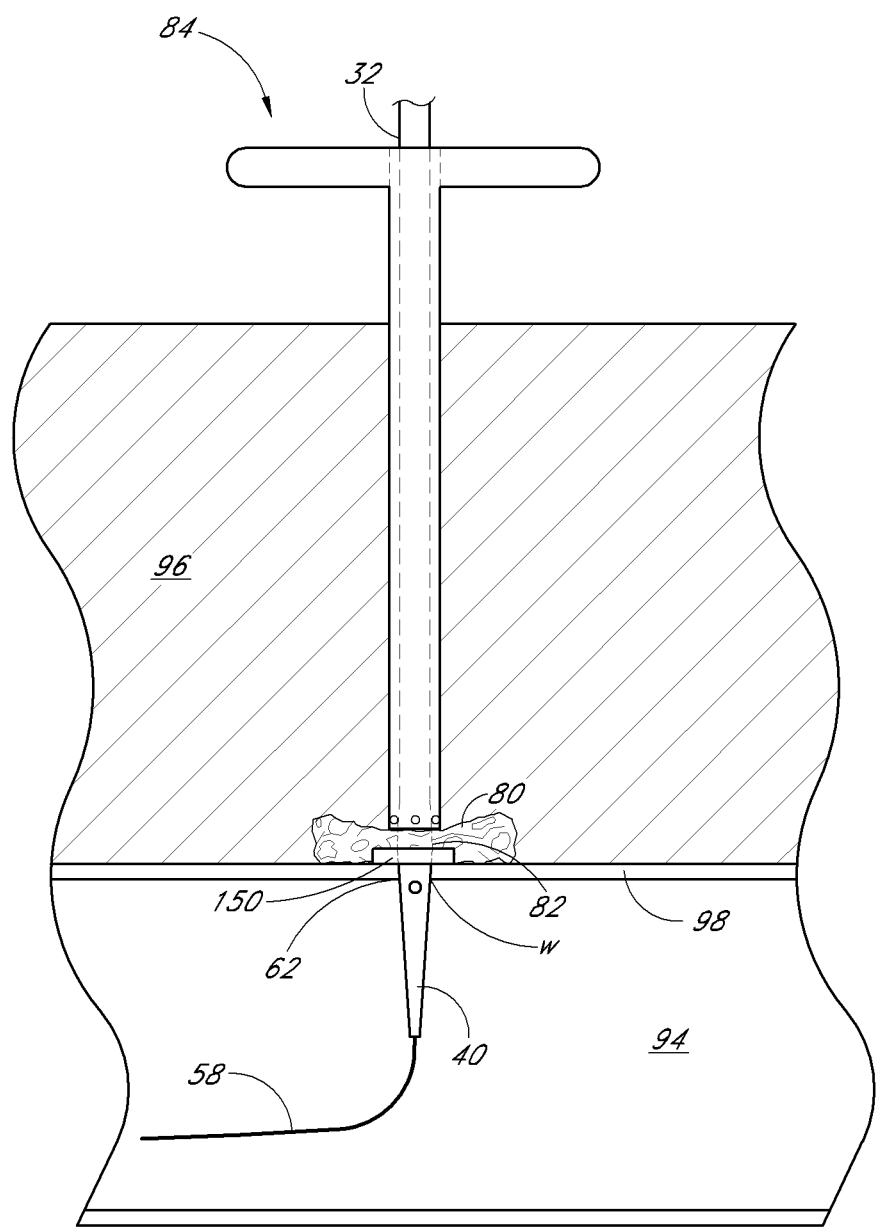
FIG. 7 shows the arrangement of FIG. 6, with the retractor arms removed.

When the sponge 80 is in place adjacent the wound w, the retractor 70 can be removed, as shown in FIG. 7. When the retractor 70 is removed, the surrounding body tissues 96 collapse around the sponge 80, blocking member, and push member 84. The push member 84 holds the sponge 80 and blocking member in position while body tissue 96 surrounds the sponge 80 and blood coagulation is initiated.

Figure 8:
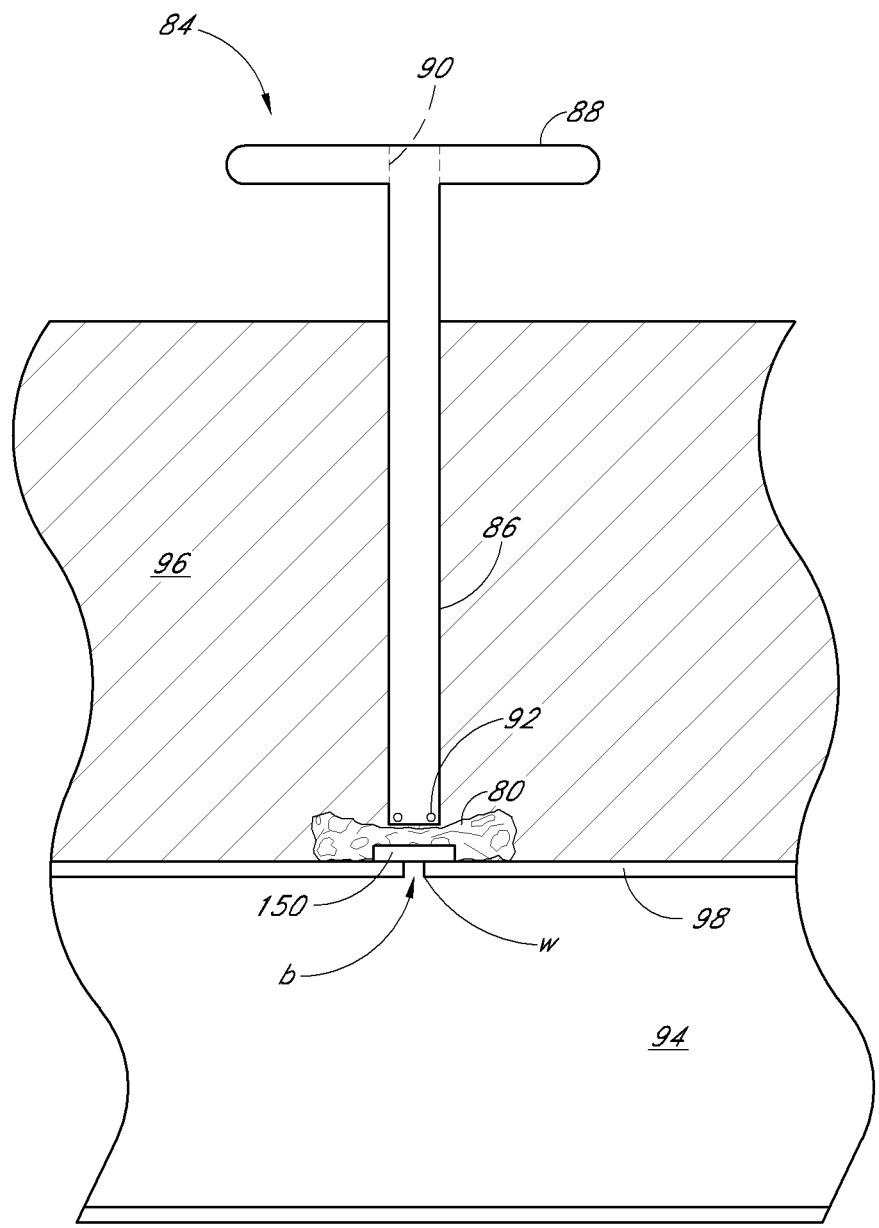
FIG. 8 shows the arrangement of FIG. 7 with the catheter and guidewire removed.

With reference next to FIG. 8, with the push member 84 in place, the catheter 32 and guidewire 58 can also be removed from the patient. The passage 82 through the sponge 80, which had been occupied by the catheter 32, preferably collapses onto itself so that it is substantially closed. The vessel wound w is no longer plugged by the catheter 32, and it is anticipated that blood b from the vessel 94 will flow into and through the blocking member 150 and further into the sponge 80, at least partially soaking the sponge 80 and blocking member 150. Although the retractor 70 is removed prior to the catheter 32 in the above-discussed embodiment, it is to be understood that, in another embodiment, the catheter may be removed prior to the retractor.

In still another embodiment, additional pressure can be applied to the push member 84 in order to at least partially block blood flow through the blood vessel 94. In this manner, the clinician can control how quickly blood will flow through the wound w and into the sponge 80. Of course, other methods and apparatus can be used to temporarily reduce or stop blood flow through the vessel.

As discussed above, the sponge 80 preferably comprises a material made of, soaked in or otherwise treated with a hemostatic agent that is specially adapted to aid blood clotting. Thus, blood that flows into the sponge encounters the agent and will quickly become clotted, causing natural sealing of the wound through blood clotting. Sponge-like hemostasis agents are available and can include products such as Gelfoam® gelatin (available from Pharmacia Corporation of Kalamazoo Mich.) and Avitene® collagen (available from C.R. Bard/Davol, Inc.). Another material that can be used as a sponge is chitosan. These and other appropriate sponges may be impregnated with agents such as thrombin, a liquid clotting agent, to help accelerate blood clot formation and Hemadex™, which is available from Medafor, Inc. Another material that may advantageously be used is an Ultrafoam® collagen sponge marketed by C.R. Bard/Davol, Inc. The Ultrafoam® sponge is made from collagen, a natural clotting agent, and does not require the addition of thrombin. This reduces preparation time and the risk that a patient will experience a potentially hazardous reaction to bovine thrombin. Other medicaments can also be included in the sponge. For example, antibiotic medicines, anti-inflammatory drugs, healing aids, and the like can be impregnated into the sponge material.

In one preferred embodiment, the hemostatic agent comprises a starch such as bioabsorbable microporous polysaccharide microspheres (e.g., TRAUMADEX™ marketed by Emergency Medical Products, Inc. of Waukesha, Wis., which employs Medafor, Inc.'s Hemadex™ porous particles). The microspheres have micro-replicated porous channels. The pore size of the microspheres facilitates water absorption and hyperconcentration of albumin, coagulation factors, and other protein and cellular components of the blood. The microspheres also affect platelet function and enhance fibrin formulation. In addition, the microspheres are believed to accelerate the coagulation enzymatic reaction rate. When applied directly, with pressure, to an actively bleeding wound, the particles act as molecular sieves to extract fluids from the blood. The controlled porosity of the particle excludes platelets, red blood cells, and serum proteins larger than 25,000 Daltons, which are then concentrated on the surface of the particles. This molecular exclusion property creates a high concentration of platelets, thrombin, fibrinogen, and other proteins on the particle surface, producing a gelling action. The gelled, compacted cells and constituents accelerate the normal clotting cascade. The fibrin network formed within this dense protein-cell matrix adheres tightly to the surrounding tissue. The gelling process initiates within seconds, and the resulting clot, while exceptionally tenacious, breaks down normally along with the microparticles. Such microporous polysaccharide microspheres, and additional hemostatic agents, are discussed in more detail in Applicants' copending application entitled "Deployable Multifunctional Hemostatic Agent," U.S. application Ser. No. 10/868,201, filed Jun. 14, 2004, the entirety of which is hereby incorporated by reference.

Any suitable hemostatic substrate can be employed as a support for the hemostatic agents of preferred embodiments. However, in a particularly preferred embodiment the hemostatic substrate comprises chitosan. Chitosan is obtained from chitin, a biopolymer obtained principally from shrimp and crab shell waste. Chitosan is the main derivative of chitin, and is the collective term applied to deacetylated chitins in various stages of deacetylation and depolymerization. The chemical structure of chitin and chitosan is similar to that of cellulose. The difference is that instead of the hydroxyl group that is bonded at C-2 in each D-glucose unit of cellulose, there is an acetylated amino group (—NHCOCH$_3$) at C-2 in each D-glucose unit in chitin and an amino group at C-2 in each D-glucose unit of chitosan.

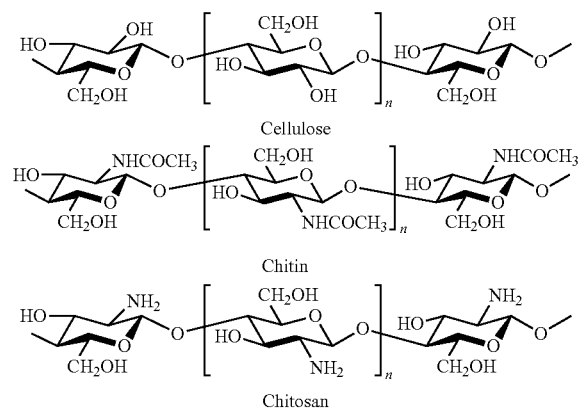

Cellulose

Chitin

Chitosan

Chitin and chitosan are both nontoxic, but chitosan is used more widely in medical and pharmaceutical applications than chitin. Chitosan exhibits good biocompatibility and is biodegradable by chitosanase, papain, cellulase, and acid protease. Chitosan exhibits anti-inflammatory and analgesic effects, and promotes hemostasis and wound healing. Chitosan has also been used as a hemostatic agent in surgical treatment and wound protection. The hemostatic effect of chitosan has been described in U.S. Pat. No. 4,394,373.

A single hemostatic substrate or combination of hemostatic substrates of different forms and/or compositions can be employed in the devices of preferred embodiments. Different substrate forms can be preferred, for example, fibrous puff, fleece, fabric, sheet, suture, powder, or the like. A homogeneous mixture of different substrate-forming materials can be employed, or composite substrates can be prepared from two or more different formed substrates. One preferred composite comprises chitosan and collagen. Additional details concerning chitosan and other suitable substrates are discussed in more detail in Applicants' copending application "Deployable Multifunctional Hemostatic Agent."

The sponge-like substrate material preferably is soft and pliable and will conform to the structure of the blood vessel, the wound and the field around the blood vessel. Thus, the sponge-like material is specially suited for use in the confined space surrounding a vascular puncture. Additionally, the hemostatic sponge 80 will be held in place by the tissue 96 surrounding the puncture wound w, which tissue 96 collapses over the sponge 80 when tools such as the retractor 70 are removed.

Figure 9:
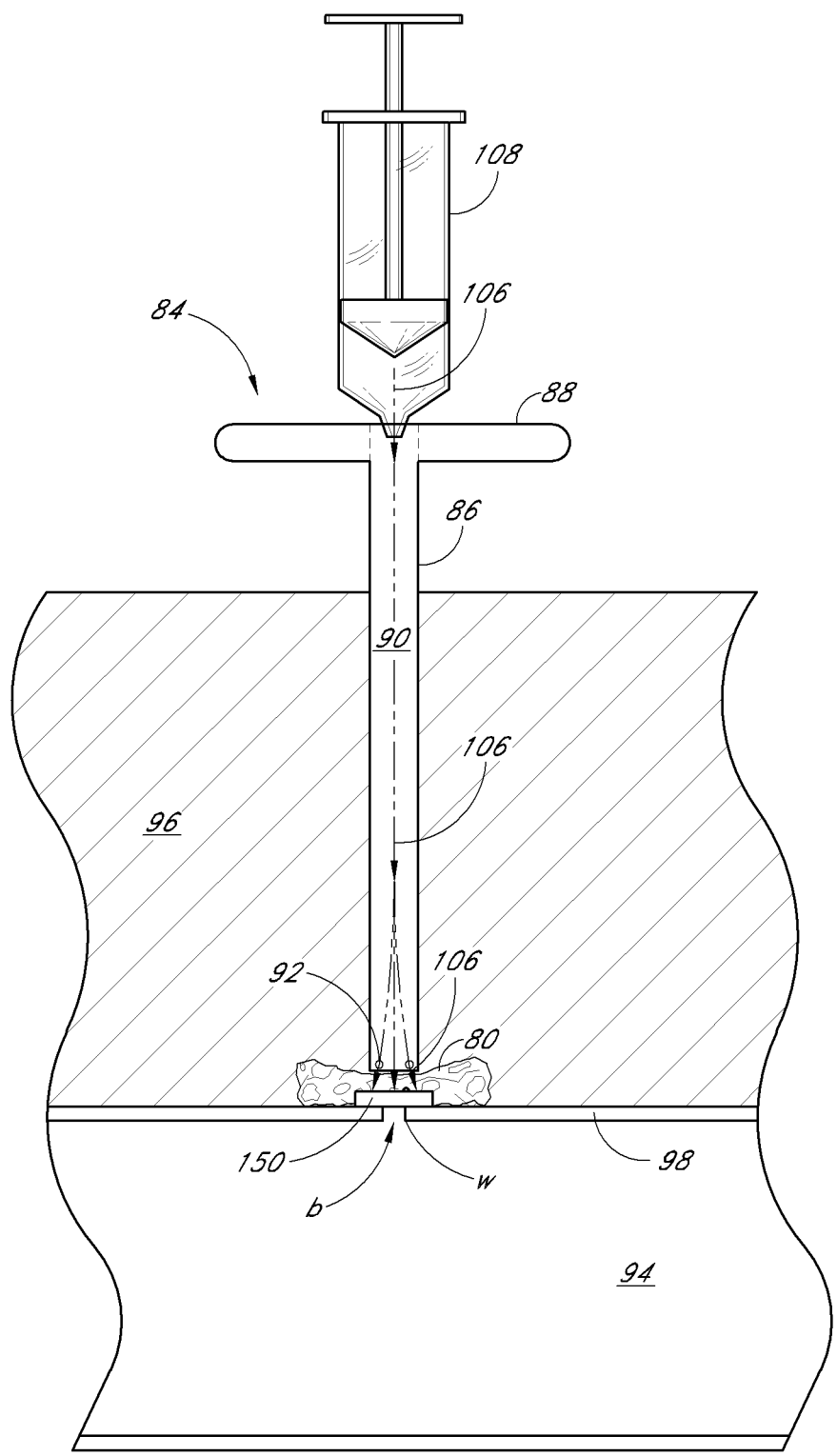
FIG. 9 shows the arrangement of FIG. 8 wherein a flowable adhesive is being delivered to the sponge.

To further help hold the sponge 80 and blocking member 150 in place, flowable adhesive 106 from a source of adhesive 108 can be delivered through the lumen 90 of the push member 84 and onto the sponge 80, as shown in FIG. 9. The adhesive 106 flows through the open distal end of the push member 84 and also through the holes 92 through the push member body portion 86. Upon curing, the adhesive 106 can form a sealing layer around and within the sponge 80 and blocking member 150, thus confining the blood b to the sponge area. This helps minimize bleeding and even further speeds clot formation. In one embodiment, adhesive, when cured, is substantially non-porous, and thus confines blood to a desired area. Adding adhesive 106 will also facilitate more complete closure of the passage through the sponge, which passage was vacated by the catheter 32. Further, the adhesive 106 will help hold the sponge 80 in place relative to the puncture wound w and the surrounding tissue 96.

In one embodiment, the sponge 80 and/or the blocking member 150 are at least partially coated with an adhesive so that the sponge 80 and/or blocking member 150 will at least partially bond to the vessel wall 98. Alternatively, or in addition, flowable adhesive can be delivered into the field 100 around the puncture wound w before the sponge and blocking member are advanced into contact with the vessel wall 98. Of course, the sponge 80 and blocking member 150 can be delivered without using any adhesive.

By controllably applying a coating of adhesive around the outer surface of the sponge 80 and blocking member 150, the adhesive will bond the blocking member 150 and sponge 80 to the area immediately surrounding the blood vessel wound w, including the vessel 94 itself. The blocking member 150 may also be adhered to the sponge 80. In a further embodiment, adhesive can form a perimeter seal of the sponge 80 when the adhesive cures. The coating of adhesive can act as a non-porous or selectively-porous membrane confining the blood b to the sponge 80 and blocking member 150. It is to be understood that a coating of adhesive may be used instead of or in addition to applying additional adhesive 106 through the push member 84.

Various kinds of flowable adhesives may be acceptable for use with the sponge. For example, fibrin tissue sealants such as Tisseel®, which is available from Baxter Healthcare Corp., may be appropriate. Other commercially available adhesives that may be appropriate include Bioglue®, available from Cryolife, Inc., and Floseal™, which is available from Baxter. Various cyanoacrylate adhesives are currently commercially available and can be used with this invention. Of course, any product that is capable of sealing the sponge or at least retarding blood flow through or beyond the sponge may be acceptable. It is also to be understood that certain adhesives will not require that the field and/or the outer wall of the blood vessel be cleared before the adhesive is injected.

Curing time and ease of use will vary depending on the adhesive used. For example, some adhesives cure to a malleable gel-like state within a few seconds, while others will cure directly to a hardened state in a few minutes. The time period for curing is chosen to allow the clinician to advance the sponge into position adjacent the wound and in contact with the artery, at which time the sponge will begin to be bonded to the vessel wall and substantially sealed by the adhesive. It should be appreciated that any acceptable adhesive having any acceptable curing time may be used. In accordance with this description, an adhesive is considered to be cured when it is adhered to surrounding tissue, and when it does not spontaneously flow.

The push member 84 may be kept in place for any reasonable time period in order to allow the adhesive 106 to cure or, in another embodiment, to allow clotting to become well established. Also, multiple sponges can be used, if desired. Preferably, however, the adhesive 106 will cure sufficiently in about five minutes or less. Other tools, such as an ultraviolet light source or a heat application device, may be used to help speed adhesive curing.

Figure 10:
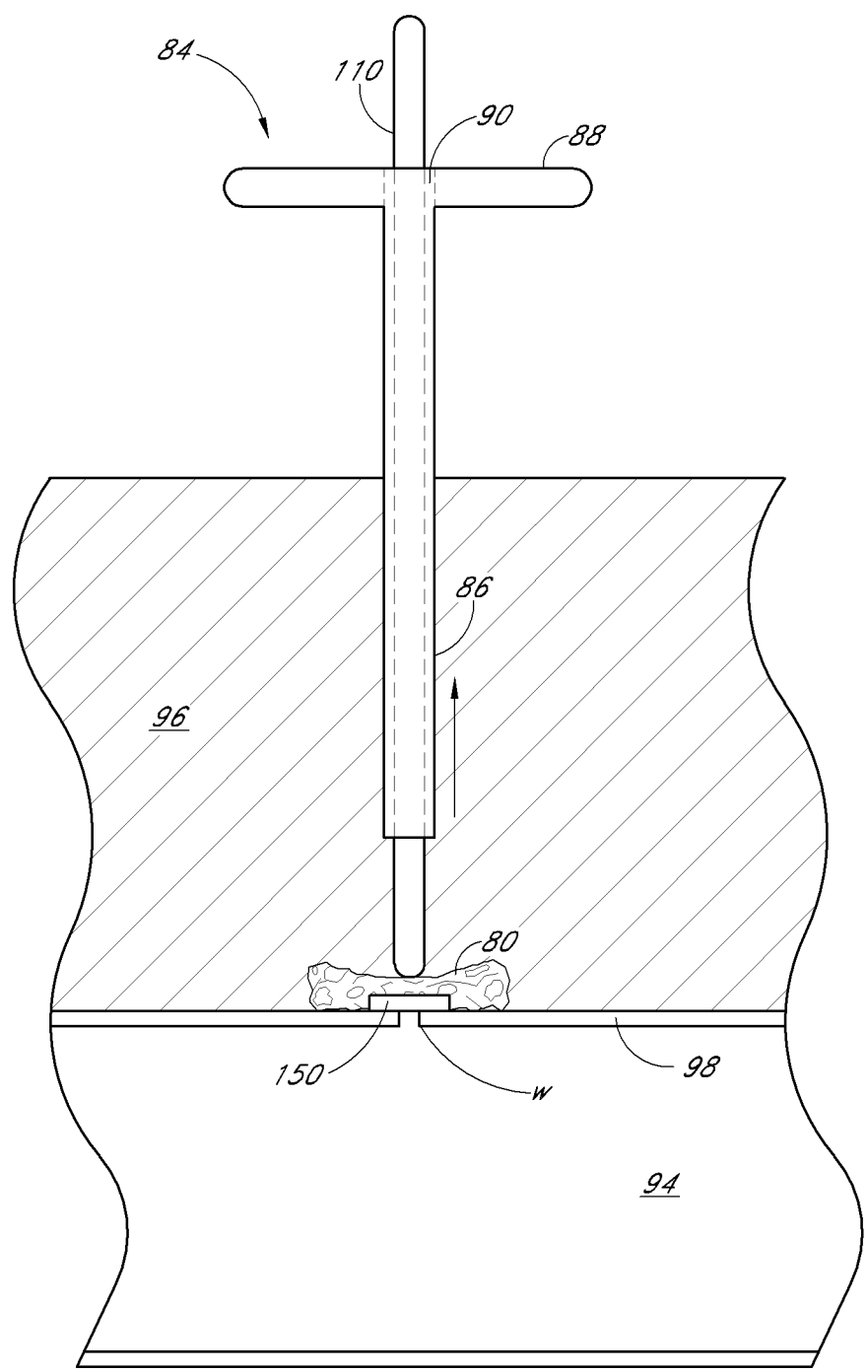
FIG. 10 shows the arrangement of FIG. 8, wherein the push member is being removed from the patient.
Figure 11:
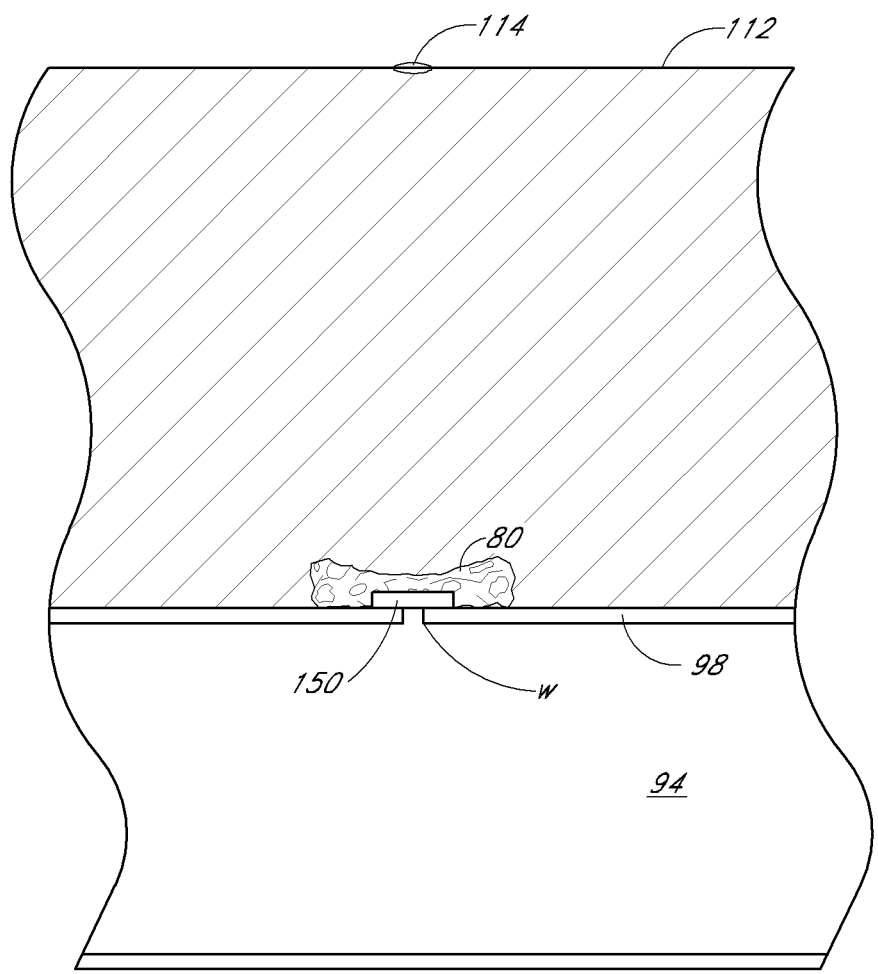
FIG. 11 shows a sealed puncture wound after treatment with an embodiment of the device and method.

Once the sponge 80 is correctly placed, the push member 84 can be removed. Removal of the push member 84 can be aided by a release rod 110 which, as shown in FIG. 10, is advanced through the push member lumen 90 and into contact with the sponge 80. The release rod 110 holds the sponge 80 in place as the push member 84 is withdrawn from the patient. Thus, the release rod 110 engages the sponge 80 so as to provide counter traction when the push member 84 is withdrawn. In this way, the push member 84 can be removed even if some adhesion occurs between the sponge 80 and the push member 84. With reference next to FIG. 11, once the release rod 110 is withdrawn, the patient's skin 112 is closed by any appropriate closure media such as, for example, sutures 114. The hemostatic sponge 80 and blocking member are in place. The body's natural blood clotting process will plug and repair the vascular wound w with the aid of the hemostatic sponge 80. Thus, healing will proceed without the danger of false aneurysms, missed or faulty wound closure, or the like.

Although certain embodiments employ adhesives in conjunction with a sponge and blocking member, it is to be understood that adhesive is not necessary in other embodiments, particularly embodiments in which the blocking member is hydrophilic, and thus tends to develop a bond with a surface at or adjacent the wound. In additional embodiments, the blocking member is adhered to the sponge prior to being advanced toward the wound. As such, the sponge and blocking member move as a unit, and portions of the sponge in contact with the blocking member are fixed in place by the adhesive, thus providing even further assurance that portions of the sponge will not advance past the blocking member and into the wound w. In a still further embodiment, the blocking member is integrally formed with the sponge.

In the embodiment illustrated in FIGS. 1-11, the catheter comprises a single-lumen catheter. In another embodiment (not shown), the elongate catheter has a first lumen comprising a tube that extends from the distal end opening to the proximal end opening and slidingly accommodates the guidewire therewithin. The outer wall of the catheter defines a second lumen that concentrically surrounds the first lumen. The holes through the outer wall of the catheter open into the second lumen. Additionally, an access lumen communicates with the second lumen. In this embodiment, the distal and proximal openings, which accommodate the guidewire, do not communicate with the second lumen, which lumen communicates with the source of suction through the access lumen. Accordingly, in this embodiment, there may be less of a chance that body fluids will be drawn into the catheter through the distal and proximal guidewire openings than in an embodiment employing a single lumen. However, the single-lumen catheter can be less expensive to manufacture and can be expected to have a smaller diameter than the dual-lumen catheter.

With reference next to FIGS. 12-25 another embodiment of a vascular wound closure assembly and method is described. In this embodiment, hemostatic material and a blocking member are enclosed within a chamber prior to delivery at or adjacent a wound to be closed.

With specific reference to FIGS. 12, 13 and 17A-B, a vascular wound closure assembly 230 includes an elongate catheter 232 having a distal end 234 and a proximal end 236. A distal opening 238 is formed through the distal end 234 of the catheter 232 and opens along a longitudinal axis of the catheter 232. The catheter 232 includes a tapered tip 240 at the distal end 234. An elongate main body 242 of the catheter 232 is disposed proximal the tapered tip 240. Preferably the main body 242 has a substantially uniform diameter along its length. A lumen 244 extends longitudinally within the catheter 232 from the distal opening 238 to the proximal end 236.

In the illustrated embodiment, a connector portion 246 is provided on the proximal end 236. The connector portion 246 includes a main lumen 248 and a secondary lumen 250. The main lumen 248 extends along the longitudinal axis of the catheter 232 and is coextensive with the catheter lumen 244. The secondary lumen 250 extends outwardly from the main lumen 248, but communicates with the main lumen 248 and the catheter lumen 244. A proximal opening 252 is provided at the proximal end of the main lumen 248 and, like the distal opening 238, opens along the longitudinal axis. A secondary opening 254 opens into the secondary lumen 250.

The distal and proximal openings 238, 252 are sized and adapted to accommodate a guidewire 258 such as the guidewire used in angioplasty and other vascular surgeries. As such, the guidewire 258 can be threaded through the catheter 232 and the catheter can be advanced over the guidewire 258.

A hole 260 is formed through a side-wall of the catheter 232 near the distal end of the catheter. In another embodiment, at least two holes are provided. All of the holes preferably are disposed substantially the same distance from the distal end of the catheter.

With continued reference to FIGS. 12, 13 and 17A-B, a vacuum or other source of suction 264 is provided and communicates, through tubing 266, with the secondary lumen 250 of the catheter connector portion 246. Thus, a vacuum is drawn through the catheter lumen 244. Preferably, the distal and proximal openings 238, 252, which accommodate the guidewire 258, are sized so that the guidewire 258 substantially plugs the openings; thus, the vacuum is drawn through the hole 260. A viewing port 268 is arranged between the source of suction 262 and the catheter 232. The viewing port 268 is configured to allow a clinician to view the material that is drawn by suction through the hole and through the catheter lumen 244.

A delivery tube 290 is disposed over the catheter 232 proximal of the hole 260. A pusher member 300 also is disposed over the catheter 232 generally proximal of the delivery tube 290. The delivery tube 290 and pusher member 300 will be discussed in more detail below. The delivery tube 290 and pusher member 300 preferably are selectively secured to the catheter 232 so that they are in a fixed position relative to the catheter. More specifically, the delivery tube 290 preferably is releasably secured to the catheter 232 so that a distal end 302 of the delivery tube 290 is spaced a distance between about 0.5 to 1.5 cm proximal of the hole 260. More preferably, the distal end 302 of the delivery tube 290 is spaced less than about 1 cm from the hole.

Figure 13:
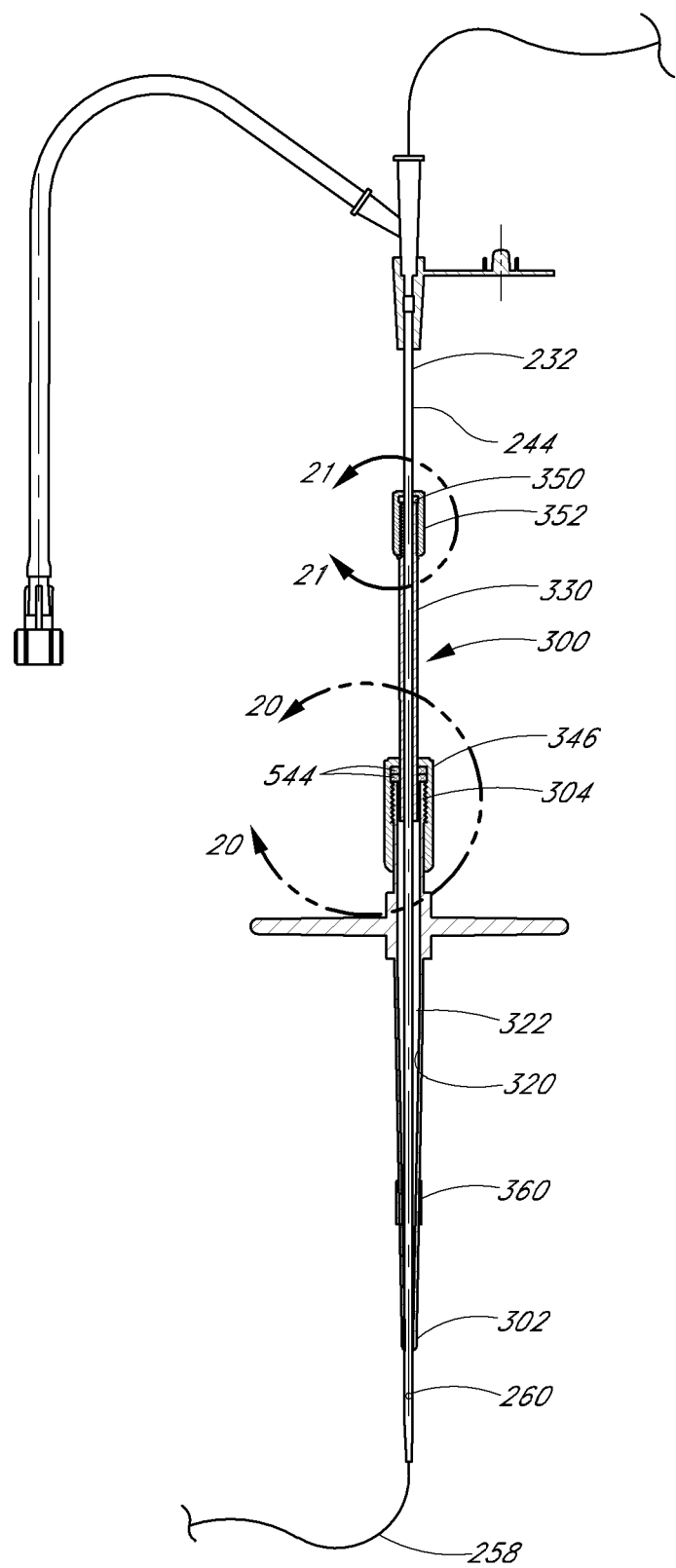
FIG. 13 is a cross-sectional view of the apparatus of FIG. 12.
Figure 14:
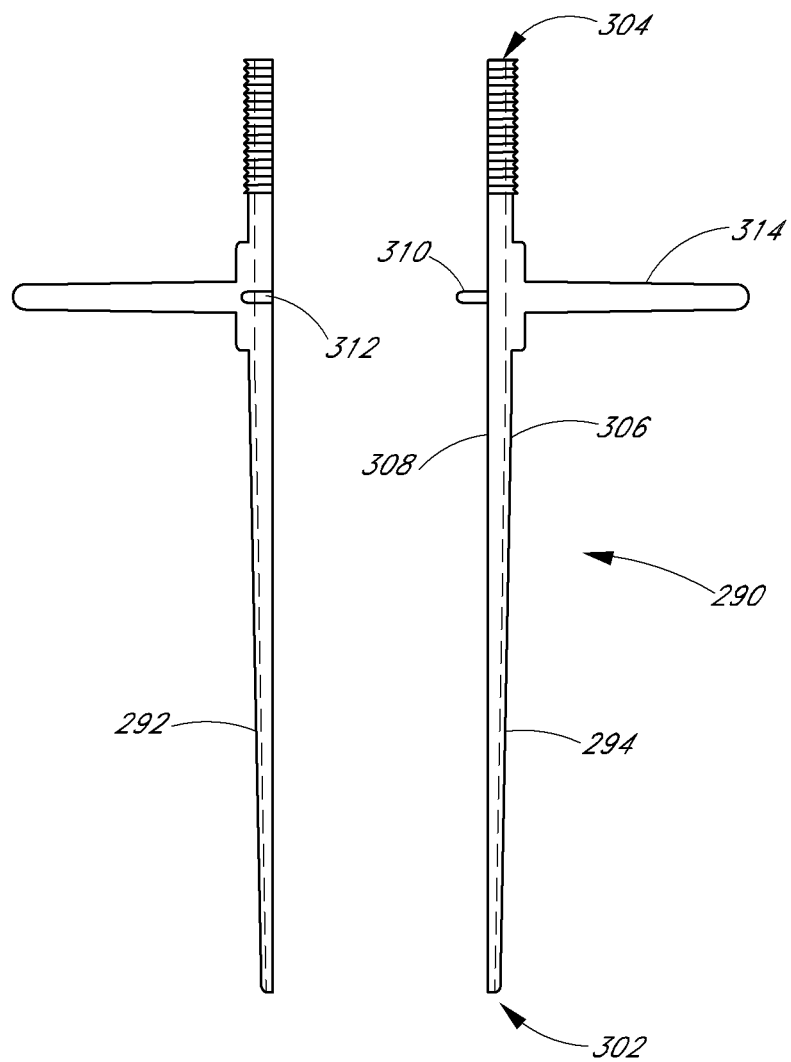
FIG. 14 shows a delivery tube portion of the apparatus of FIG. 12 separated into halves.

With reference next to FIG. 14, the delivery tube 290 is generally elongate and comprises first and second separately-formed members 292, 294 that engage one another to form the delivery tube 290. Each tube member 292, 294 has a distal end 302, a proximal end 304, an outer surface 306 and an inner surface 308. Guide posts 310 formed on one of the tube members 292, 294 fit into guide recesses 312 formed in the other member so as to align the tube members 292, 294. When connected and aligned as shown in FIG. 13 the tube members 292, 294 form the delivery tube 290.

As shown, the proximal end 304 of the delivery tube 290 preferably is threaded on its outer surface 306. A handle portion 314 is disposed distal of the proximal end 304, and the delivery tube 290 generally tapers from the handle 314 to the distal end 302.

With continued reference to FIGS. 13 and 14, a chamber 320 is formed within the delivery tube 290, and the catheter 232 extends therethrough. At the distal end 302 of the delivery tube 290, the chamber 320 is just large enough to accommodate the catheter 232. However, as the tube tapers in a proximal direction, a space 322 is defined between the catheter 232 and the inner surface 308 of the tube 290.

Figure 15:
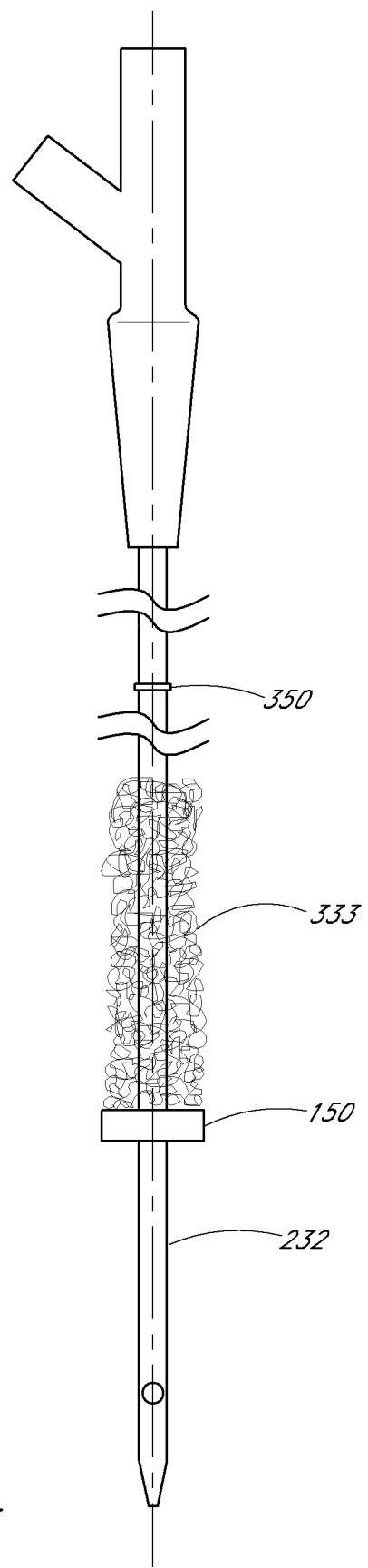
FIG. 15 shows an embodiment of a catheter portion adapted for use with the apparatus of FIG. 12.

With specific reference next to FIG. 15, preferably a therapeutic agent is disposed within the space 322 on and circumferentially around the elongate catheter 232. In the illustrated embodiment, the therapeutic agent is a hemostatic material 333 comprising a hydrophilic fibrous fleece. Preferably, a blocking member 150 is arranged on the catheter 232 distal of the hemostatic material 333. The blocking member 150 is configured to have an outer diameter substantially greater than that of a puncture wound w to be closed, and to have an inner diameter generally corresponding to the outer diameter of the catheter 232 to substantially establish a seal between the blocking member 150 and the catheter 232 so that the hemostatic material 333 cannot work its way distally between the blocking member 150 and catheter 232. Nevertheless, preferably the blocking member 150 is adapted to be slidable over the catheter 232.

In a preferred embodiment, the hemostatic material 333 comprises a hydrophilic fibrous fleece. Throughout this description, the term fleece is used as a broad term in its ordinary sense and refers, without limitation, to fibrous material arranged in a non-woven or a woven cloth form or in a loosely arranged puff or ball form. It is to be understood that the fibrous fleece may be treated or coated in any suitable manner to enhance its hydrophilic properties and/or its hemostatic properties. In a preferred embodiment, fibrous chitosan fleece is treated to deposit a hemostatic agent thereon. For example, in one embodiment microporous polysaccharide microspheres are deposited on the fleece. For purposes of this specification, a fleece can be considered a type of sponge.

Figure 16:
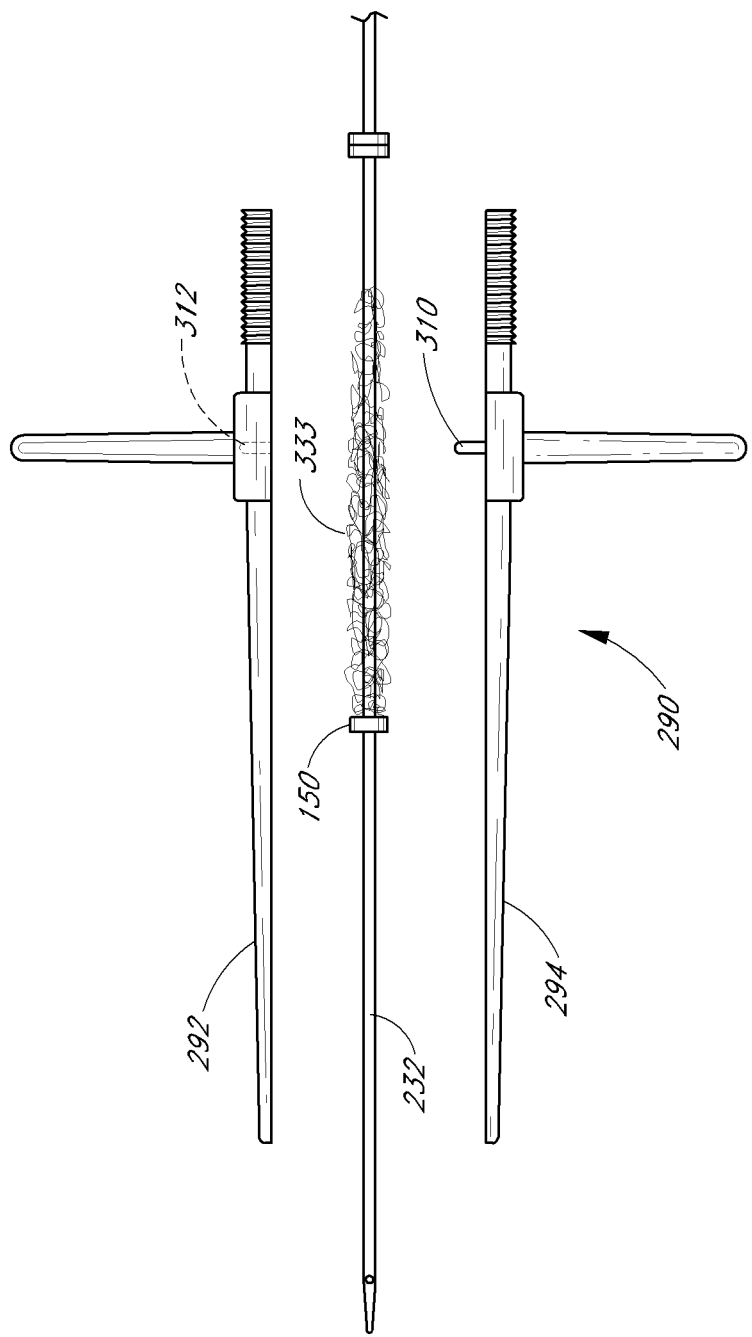
FIG. 16 shows the catheter portion of FIG. 15 arranged between two halves of a delivery tube portion.

With specific reference also to FIGS. 16 and 17A, to assemble the delivery tube 290 in accordance with one embodiment, preferably the fibrous hemostatic material 333 and blocking member 150 are arranged on the catheter 232 and the catheter 232 is positioned between the first and second members 292, 294 of the delivery tube 290. The tube members 292, 294 are aligned and connected to form the delivery tube 290. In this manner the delivery tube 290 is assembled with the catheter 232, blocking member 150, and hemostatic material 333 arranged therein. Preferably, and with specific reference also to FIG. 13, a distal end 328 of the pusher member 300 is accommodated within the proximal end 304 of the delivery tube 290.

With specific reference to FIGS. 17A and 18, the catheter 232 preferably is arranged relative to the delivery tube 290 so that the blocking member 150 is proximal the distal end 302 of the tube 290. As discussed above, the tube 290 generally tapers from the handle 314 to the distal end 302. Correspondingly, the inner surfaces 308 of the tube taper so that the space 322 between the catheter 232 and inner surface 308 steadily increases moving proximally. Since, as discussed above, the blocking member 150 preferably has an outer diameter greater than the diameter of the puncture wound w, the blocking member 150 is too large to fit within the chamber 320 at the distal end 302 of the tube 290. However, preferably the blocking member 150 is arranged at a position along the tube so that the outer diameter of the blocking member 150 fits snugly against the inner surface 308 of the closed tube 290. Most preferably, the blocking member 150 creates a seal with the tube inner surface 308 so that hemostatic material 333 remains proximal of the blocking member 150 and is blocked from working its way distal of the blocking member 150.

As discussed above, there are various types and forms of hemostatic material that may be used in accordance with preferred embodiments. For example, in another embodiment, the hemostatic material may comprise collagen configured in a gel-like state. In such an embodiment, to assemble the delivery tube, 290 the blocking member 150 preferably is first arranged on the catheter 232, the catheter is positioned between the first and second members 292, 294 of the delivery tube 290, and the tube members are aligned and connected to form the delivery tube 290. The catheter 232 and blocking member 150 preferably are arranged so that the perimeter surface 158 of the blocking member 150 sealingly engages the inner surfaces 308 of the tube members 292, 294, thus establishing a seal within the chamber 320. Collagen is then inserted through the proximal end 304 of the tube 290. The collagen preferably substantially fills the tube 290 proximal of the blocking member 150, but is prevented from progressing distally beyond the blocking member 150.

Figure 19:
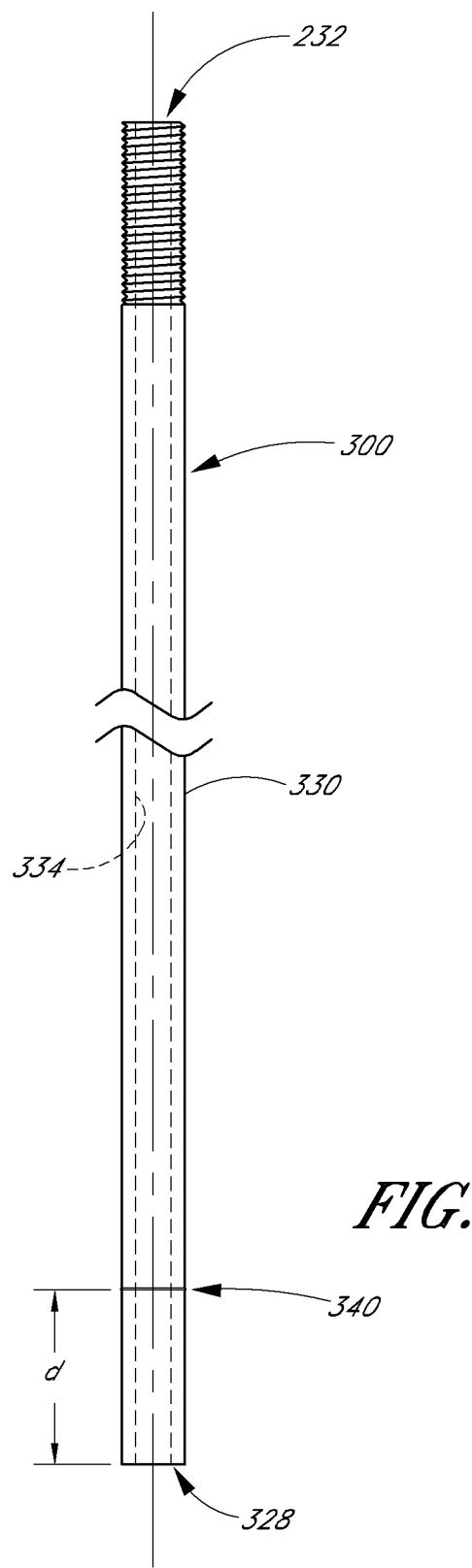
FIG. 19 shows a pusher member of the apparatus of FIG. 12.

With reference next to FIG. 19, the pusher member 300 comprises an elongate body 330 and has distal and proximal ends 328, 332. A lumen 334 is formed longitudinally through the pusher member 300, and preferably is sized to slidably accommodate the catheter 232 therethrough. Preferably, the pusher member 300 is rigid enough so that it can be grasped at or near its proximal end 332 and pushed forward, in turn engaging and pushing the hemostatic material 333 and blocking member 150 within the delivery tube 290 without binding or bending excessively.

The distal portion 328 of the pusher member 300 is configured to fit within a proximal portion 304 of the delivery tube 290. However, the distal portion 328 of the pusher member 300 preferably has a greater diameter than at least a portion of the delivery tube 290 near the distal end 302 of the delivery tube 290. As such, when the pusher member 300 is advanced relative to the delivery tube 290, the pusher member 300 engages the inner surfaces 308 of the tube members 292, 294 and forces them apart so as to deploy the hemostatic material 333 from within the delivery tube 290.

In a preferred embodiment, since the blocking member 150 has an outer diameter greater than the portion of the delivery tube chamber 320 distal of its position, when the pusher member 300 advances the hemostatic material 333 and blocking member 150 distally, the blocking member 150 engages the inner surface 308 of the tube members 292, 294 and forces them apart. In a preferred embodiment, the pusher member 300 has a greater outer diameter than the blocking member 150 so that the pusher member 300 forces the tube members 292, 294 apart at a point proximal of the location at which the pusher member 150 forces the tube members 292, 294 apart. In yet another embodiment, the pusher member has a smaller diameter than the blocking member.

In the illustrated embodiment, the pusher member 300 is threaded along its proximal end 332. An annular ridge 340 is formed a distance "d" from the distal end 328 of the pusher member 300. The annular ridge 340 projects radially outwardly a very small distance from an outer surface of the pusher member 300. Since the annular ridge 340 projects only a very small distance from the surface of the pusher member 300, it does not interfere with the pusher member's slidability into the proximal end 304 of the delivery tube 290.

In the illustrated embodiment, the pusher member 300 has a diameter of about 4 mm and a lumen diameter 334 of about 2 mm. The annular ring 340 extends outwardly from the outer surface a distance of between about 0.1 mm to 0.25 mm, and, more preferably, about 0.15 mm.

Figure 20:
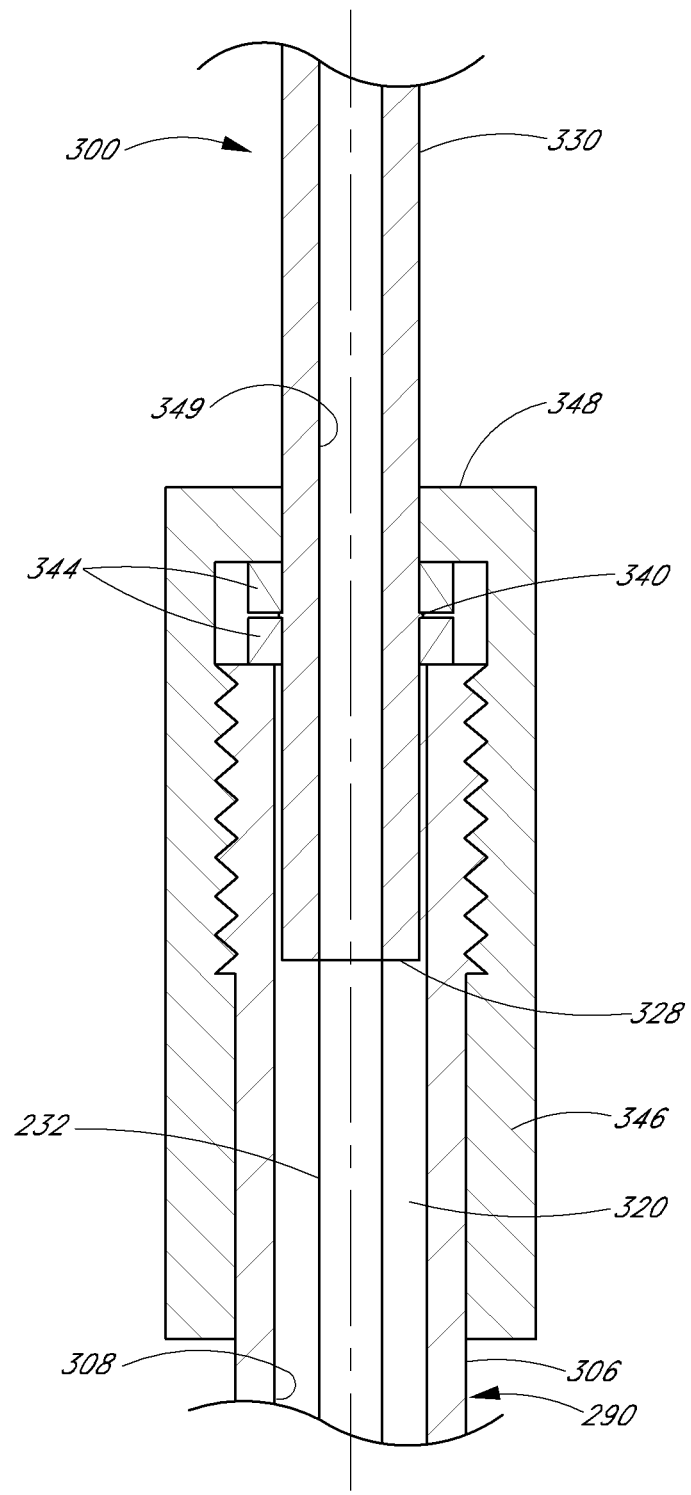
FIG. 20 is a close up view taken along lines 20-20 of FIG. 13.

With reference also to FIG. 20, which shows a close up view of the distal portion 328 of the pusher member 300 as installed on the delivery tube 290, preferably a pair of elastomeric annular locking members 244 are disposed around the pusher member 300. The locking members 344 preferably are arranged immediately adjacent either side of the annular ridge 340, and are sized so as to engage the proximal end 304 of the delivery tube 290 so as not to slide into or over the delivery tube 290. Preferably, the elastomeric locking members 344 are fit about the pusher members 300 so that they can be slid along the pusher member 300, and even can slide over the annular ridge 340.

An internally threaded locking cap 346 is configured to be threaded onto the proximal end 304 of the delivery tube 290. The locking cap 346 has proximal wall 348 having a hole 349 formed therethrough. The hole 349 is sized to accommodate and slide over the pusher member body 330. As shown, the locking members 344 are arranged on the pusher member body 330 adjacent either side of the annular ridge 344, and the pusher member 300 is inserted into the delivery tube 290 until the locking members 344 engage the proximal end 304 of the delivery tube 290. The cap 346 is then advanced over the pusher member 300 and threaded into place on the delivery tube 290. As the cap 346 is tightened, the proximal wall 348 of the cap 346 engages the locking members 344, which are then compressed longitudinally between the cap proximal wall 348 and delivery tube proximal end 304. Due to their elastomeric properties, as the locking members 344 are compressed longitudinally, they expand laterally, and thus tightly engage the pusher member 300 at and adjacent the annular ridge 344.

In the illustrated embodiment, the locking members 344 tightly engage the annual ridge 340 such that they resist sliding over the ridge. Since a locking member 344 is disposed on each side of the ridge 340, the pusher 300 is thus prevented from sliding in either a proximal or a distal direction relative to the tube 290. However, once the cap 346 is loosened and the locking members 344 are released from compression, the annular ridge 340 is slidable through the locking members 344, and the pusher 300 is correspondingly slidable.

In the illustrated embodiment, the locking cap 346 and delivery tube 290 are threaded. It is to be understood that any other fastening mechanism may be employed, such as for example a Mock or detent.

The illustrated embodiment employs an annular ridge 340 disposed on the pusher member 300. It is to be understood, however, that other configurations employing a similar principle can be acceptable. For example, any type of protuberance, including a bump, a series of bumps, spikes or any other protuberance that projects from a surface of the pusher member 300 can be employed. Further, protuberances can be employed at only one area disposed a predictable distance from the distal end of the pusher member as shown in the illustrated embodiment, or, in other embodiments, can be disposed at various locations or even continuously along the pusher member so as to allow customization and optimization of the placement and locking position of the pusher member relative to the delivery tube. Further, in other embodiments, rather than a series of bumps or the like, the pusher member surface can be treated to create a surface roughness, such as by being sanded with a low grit sandpaper, or to be pitted. In such an instance, protuberances are considered to extend from the lowest portions of the pits, grooves or the like. When the locking members 344 are longitudinally compressed, the locking members will expand transversely and tightly engage at least portions of the pits and protuberances so as to fix the pusher member 300 in position relative to the delivery tube 290. As such, a protuberance is considered to be any surface aspect upon which a locking member may obtain purchase to grip the pusher member when the cap is tightened.

In the illustrated embodiment, the locking members 344 comprise elastomeric rings. It is to be understood that, in other embodiments, the locking members may be shaped differently, and may extend around only a portion of the pusher member. Further, although the illustrated embodiment shows two locking members 344 disposed one on either side of the annular ridge 340, it is to be understood that other embodiments may employ only a single locking member, or more than two locking members, configured to releasably engage an annular ridge or other protuberance configuration. In still another embodiment, one or more locking members are employed, but no protuberances are formed on the pusher member surface. In this embodiment, the locking members are pushed tightly against the pusher member when the cap is tightened so as to increase the friction between the locking members and the pusher member, and accordingly resist movement of the pusher member relative to the delivery tube.

Figure 17B:
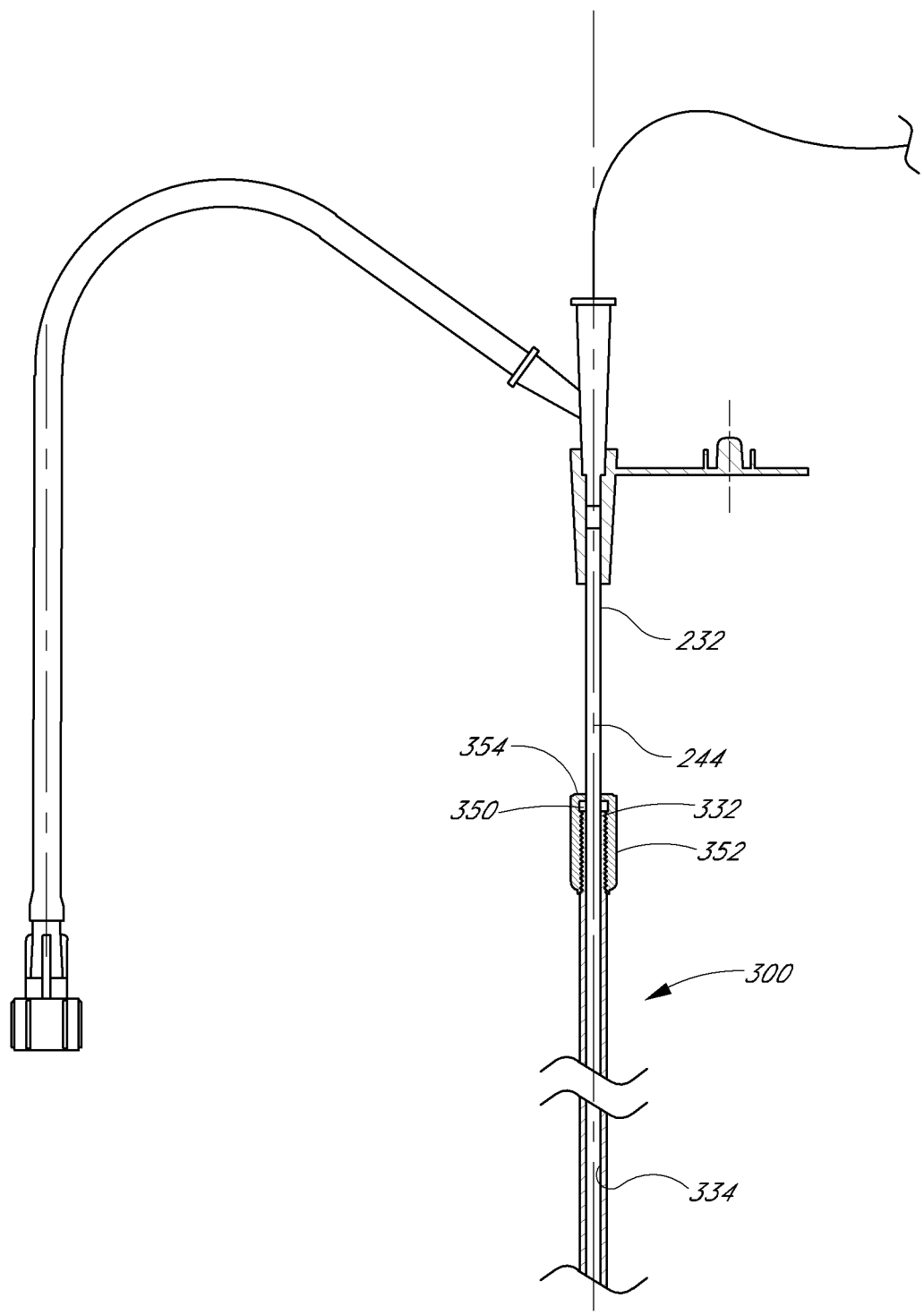
FIG. 17B is a close up view of another portion of the apparatus of FIG. 12.
Figures 21, 22:
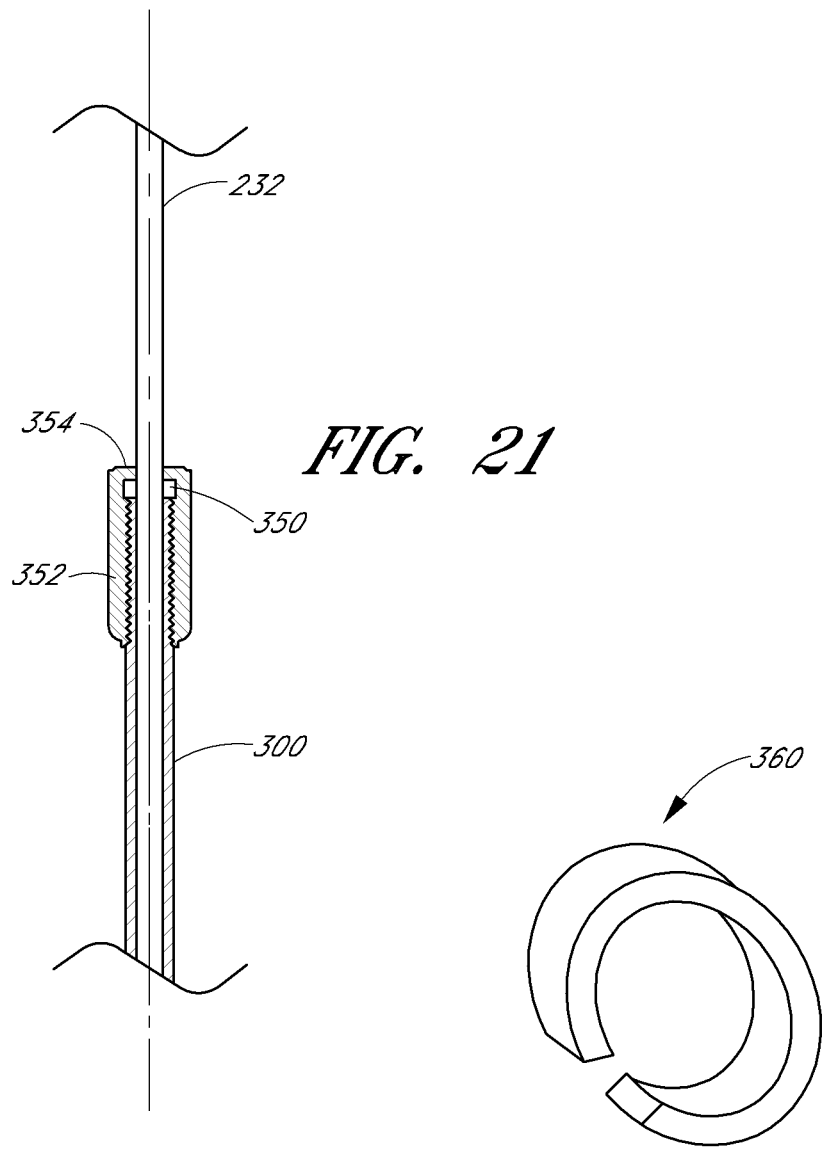
FIG. 21 is a close up view taken along lines 21-21 of FIG. 13.
FIG. 22 is a perspective view of a collar portion for use with the apparatus of FIG. 12.

With reference again to FIG. 15, the catheter 232 preferably comprises a stop member 350 extending radially outwardly from the catheter surface. In the illustrated embodiment, the stop member 350 comprises an annular ring; however, it is anticipated that any sort of protuberance can be employed. With reference also to FIGS. 17B and 21, a coupling member 352 preferably is movably disposed about the catheter 232 and is configured to mechanically couple to the proximal end 332 of the pusher member 300.

In the illustrated embodiment, the coupling member 352 is threaded on its inner surface in order to engage the threaded proximal end 332 of the pusher member 300. When the coupling member 352 and pusher member 300 are engaged, the catheter stop member 350 is locked between the proximal end 332 of the pusher member 300 and a proximal wall 354 of the coupling member 352. As such, the catheter 232 is selectively fixed in position relative to the pusher member 300. As discussed above, the pusher member 300 is selectively fixed in position relative to the delivery tube 290. As such, when the locking cap 346 and coupling member 352 are engaged as discussed above, the catheter 232, pusher member 300 and delivery tube 290 are all in fixed positions relative to one another.

In another embodiment, the catheter 232 comprises a protuberance, such as an annular ring, and one or more locking members are provided so as to releasably secure the pusher member 300 to the catheter 232 when the coupling member 352 is engaged.

With reference next to FIG. 22, a collar 360 is illustrated. The illustrated collar 360 preferably is made of a polymer formed as a broken ring. As such, the collar 360 is resilient and circumferentially expandable.

With reference also to FIGS. 12, 13 and 23-25, the collar 360 preferably is configured to fit about the delivery tube 390. A relaxed diameter of the collar 360 is less than the diameter of at least most of the tapered portion of the delivery tube 290. Thus, the collar 360 is circumferentially expanded in order to fit over the delivery tube 290. Such circumferential expansion is resisted by the collar 360 so that the collar 360 exerts an inwardly-directed force on the delivery tube 290.

In order to ease advancing of the tube through tissues, the outer diameter of the delivery tube 290 is made quite small. As a result, the walls of the tube members 292, 294 preferably are quite thin. In some embodiments, the thin-walled tube members are somewhat flexible. The inwardly-directed force exerted by the collar 360 helps hold the tube members 292, 294 together so as to fit closely about the catheter 232 and to contain the hemostatic material 333 within the chamber 322. In one embodiment, the collar is initially fit onto the delivery tube at a location corresponding to or distal to the position of the blocking member within the tube. The inward force provided by the collar helps keep the tube closed and helps improve the seal between the blocking member and the inner surface.

In the illustrated embodiment, the collar 360 is configured to be slidable over the delivery tube 290. Preferably both the collar 360 and the delivery tube 290 have smooth engaging surfaces. It is to be understood that other surface configurations can be used as appropriate.

Figure 23:
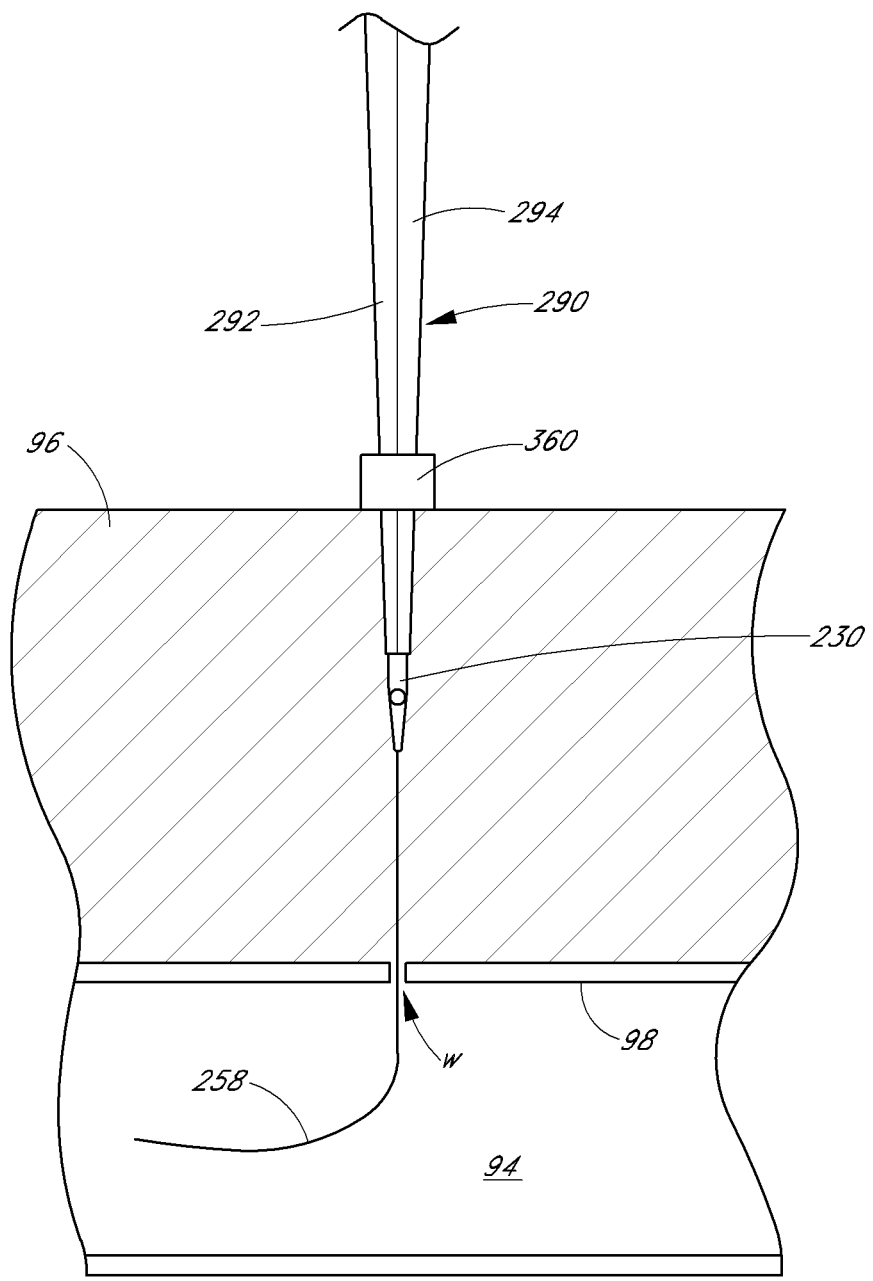
FIG. 23 shows a portion of the apparatus of FIG. 12 being advanced toward a tissue wound.
Figure 24:
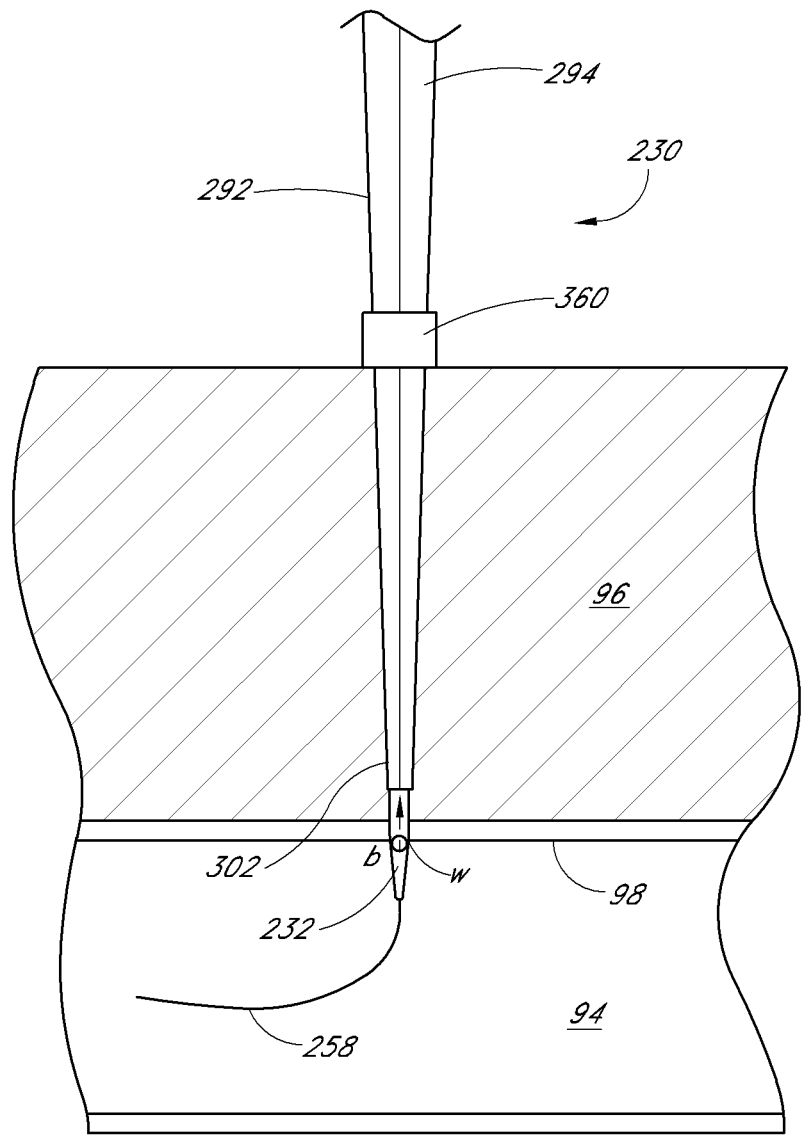
FIG. 24 shows a portion of the apparatus of FIG. 12 in position adjacent a vascular wound.

The illustrated vascular wound closure assembly 230 can be precisely positioned adjacent a subcutaneous vascular wound "w" in order to close the wound. With specific reference to FIGS. 12 and 13, in order to precisely locate and provide access to a femoral artery puncture wound w, the catheter 232 is first threaded over the guidewire 258, which has been previously inserted into the patient's femoral artery 94 through the puncture wound w. As best shown in FIGS. 23-24, with the lumen 244 attached to the source of suction 264, the assembly 230 is advanced over the guidewire 258 through a patient's tissue 96 so that the distal tip 240 of the catheter 232 extends through the vascular puncture wound w.

As the assembly 230 is advanced, the source of suction 264 draws bodily fluids through the hole 260. The fluids pass through the viewing port 268, which allows the clinician to identify the fluids being withdrawn. The viewing port 268 can have any suitable structure or location. For example, the viewing port can comprise clear tubing attached to the catheter, a substantially transparent syringe that functions as both a source of suction and a viewing port, or a portion of the catheter that is substantially transparent. Most preferably, the catheter 232 is formed of a transparent material so that the clinician becomes aware as soon as blood begins to be drawn through the catheter.

As the apparatus 230 is advanced, the collar 360 engages the patient's skin, as shown in FIG. 23. As the apparatus is further advanced, the collar 360 continues to engage the patient's skin and the delivery tube 290 slides distally relative to the collar 360, as shown in FIG. 24. The collar expands with the diameter of the tapered delivery tube 290 as the tube slides relative to the collar 360, and the collar continues to exert an inwardly-directed circumferential force to help hold the tube closed. It is anticipated that the body tissue 96 surrounding the portion of the delivery tube 290 distal of the collar 360 also helps to keep the tube closed.

When the hole 260 passes the artery wall 98 and enters the blood vessel 94, as shown in FIG. 24, blood "b" begins to be drawn through the hole 260 into the catheter 232 and is conducted past the viewing port 268. Thus, when blood b is observed in the viewing port 268, the clinician will know that the hole 260 has just passed into the puncture wound w and that the distal end 302 of the delivery tube 290 thus positioned adjacent the outer wall 98 of the artery 94, preferably within about 1 cm of the artery wall 98.

Figure 25:
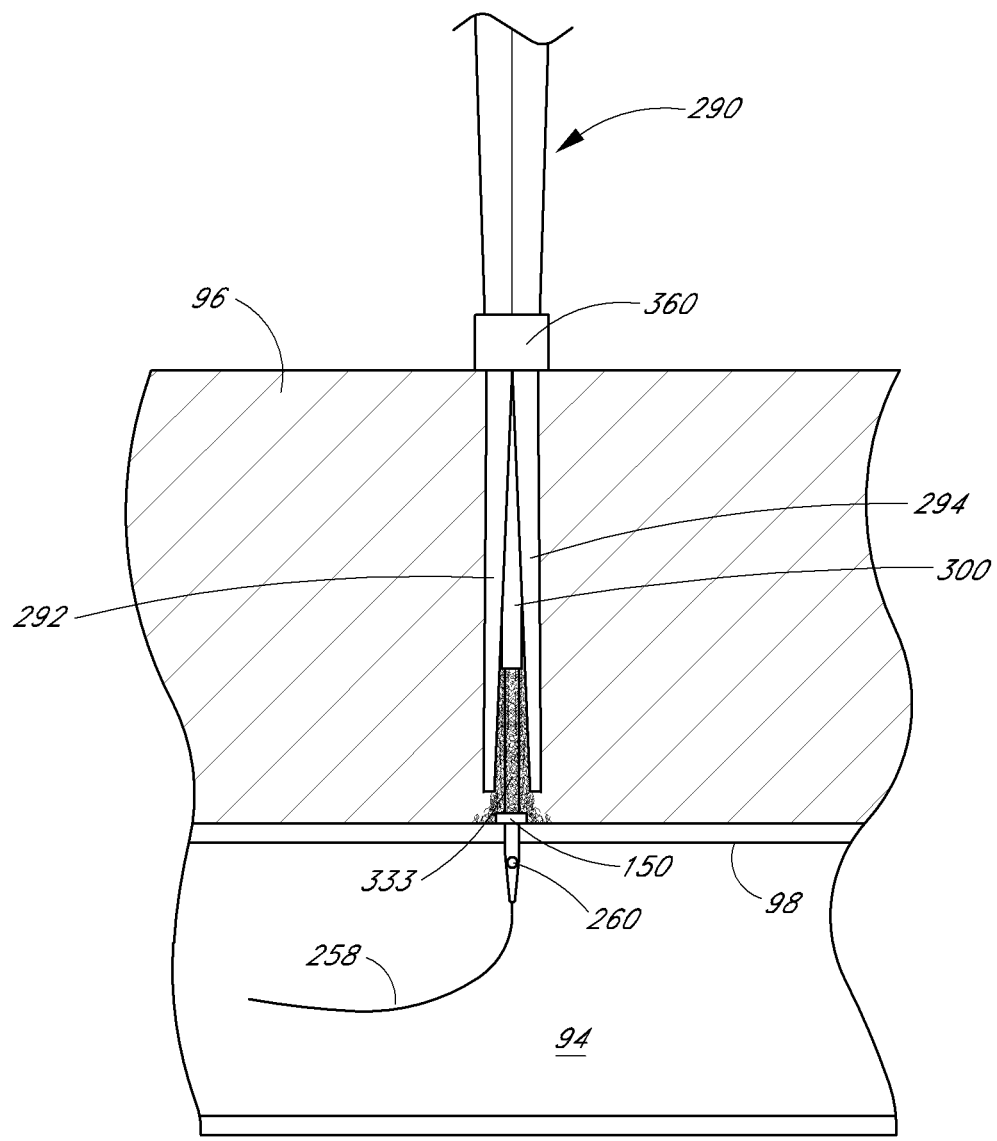
FIG. 25 shows the arrangement of FIG. 24 with the apparatus in position adjacent the wound and deploying a hemostatic agent.

When the apparatus 230 is in a desired position at or adjacent a wound w, as shown in FIG. 24, the coupling member 352 and cap 346 are disengaged so that the pusher member 300 can be advanced relative to the delivery tube 290 and catheter 232. With particular reference to FIG. 25, as the pusher member 300 is advanced, the distal end 328 of the pusher member 300 and/or the perimeter surface 158 of the blocking member 150 engages inner surfaces 308 of the tube members 292, 294, thus forcing the tube members 292, 294 apart and deploying the hemostatic material 333 and blocking ring 150 from within the delivery tube chamber 322. In the embodiment illustrated in FIG. 25, the tube members 292, 294 are flexible so that they will bend outwardly upon urging from the advancing pusher member 300 and blocking ring.

As discussed above, in one embodiment, the hemostatic material 333 comprises a hydrophilic fibrous chitosan fleece and the blocking ring 150 comprises a hydrophilic fibrous, yet relatively dense, chitosan cloth. Since the fleece and blocking member are hydrophilic, they will stick to the blood vessel 98 surrounding the wound w and to surrounding body tissues 96. Further, none of the fibrous material passes through the wound into the blood vessel 94. As the catheter 232 is removed from the wound w, the fleece readily collapses into the space previously occupied by the catheter. The fleece 333 has hemostatic properties, and fully surrounds the wound w, thus aiding relatively quick hemostasis of the wound.

In some embodiments the closure device 230 is assembled so that the distance from the catheter hole 260 to the distal end 302 of the delivery tube 290 is about or slightly greater than the width of a blood vessel wall 98. As such, the delivery tube 290 is arranged immediately adjacent the wound w. With continued reference to FIGS. 24 and 25, in the illustrated embodiment, the distance from the catheter holes 260 to the distal end 302 of the delivery tube 290 is much greater than the width of a blood vessel wall 98, but less than about 1.5 cm. More preferably the distance is about 1 cm or less. As such, when the catheter holes 260 enter the blood vessel 94 and the clinician sees blood enter the viewing port 268, the delivery tube 290 is positioned close to, but spaced from the vessel wall 98. In the illustrated embodiment, this spacing provides a safety feature to ensure that the distal ends 302 of the delivery tube members 292, 294 do not enter or damage the wound site w. Upon deployment of the hemostatic material 333, the pusher member 300 pushes the material 333 and blocking member 150 over the catheter 232 and into contact with, or into close proximity to, the vessel wall 98 and the wound w. In accordance with another embodiment, the delivery tube 290 is spaced from the vessel wall 98 a distance of at least about three times the thickness of the vessel wall.

With continued reference to FIG. 25, when the tube members 292, 294 are expanded upon deployment as illustrated, there is further resistance to distal movement of the tube members 292, 294, thus further contributing to safety. Still further, although the collar 360 is slidable over the delivery tube 290, it contributes some frictional resistance to further distal movement of the delivery tube 290 relative to the collar 360.

Several types of materials can be used to construct the blocking member 150. Such materials may or may not have advantageous hemostasis-promoting properties. For example, elastic, non-elastic, natural and man-made materials, and combinations thereof, can be used. Polymer materials taken alone or in combination with a hemostatic agent and/or adhesive may be employed. Preferably, the blocking member is constructed from a biodegradable material such as polylactic acid (PLA), chitosan, or other biodegradable materials. Another preferred class of suitable materials includes materials that may be used for vascular grafts. Still another preferred material for constructing a blocking member comprises Gore-Tex®, which is available from W. L. Gore and Associates, Inc.

In a preferred embodiment, the blocking member 150 may be a fibrous non-woven chitosan fabric. Due to its hydrophilic nature, the chitosan blocking member preferably will adhere to the outer surface 98 of the blood vessel 94. This further secures the blocking member in place on the blood vessel so as to prevent entry of any loose hemostatic material into the blood vessel. Additionally, a chitosan blocking member can take advantage of the advantageous hemostasis-promoting properties of chitosan and will assist in promoting blood clotting to close the wound.

In some embodiments, the blocking member is rigid or semi-rigid, either due to the material used or due to a relatively high density. As such, the blocking member will not deform under pressure to the point that hemostatic material can pass distally by the blocking member and into the wound. In other embodiments, the blocking member is generally flexible. As such, it more easily conforms to the shape of the blood vessel 94. In such embodiments, the blocking member preferably has an outer diameter sufficient so that the blocking member cannot fit through the wound w.

In yet another embodiment, the blocking member is constructed of a mesh material comprising a mesh fine enough to prevent fibrous hemostatic material from passing through the mesh, yet will facilitate passage of blood therethrough and into the hemostatic material. In one embodiment, the mesh is substantially rigid and thick so as to maintain structural rigidity and spacing from the wound w to enhance safety of the device. In another embodiment, the mesh is malleable to promote easier use, but the mesh is strong and will not break under operating pressures, so that it will maintain its sturdy construction to prevent portions of the hemostatic material 333 from passing through the mesh and into the wound w.

Figure 26:
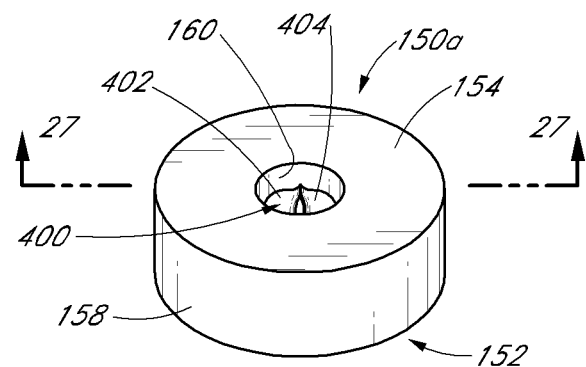
FIG. 26 is a perspective view of another embodiment of a blocking member.
Figure 27:
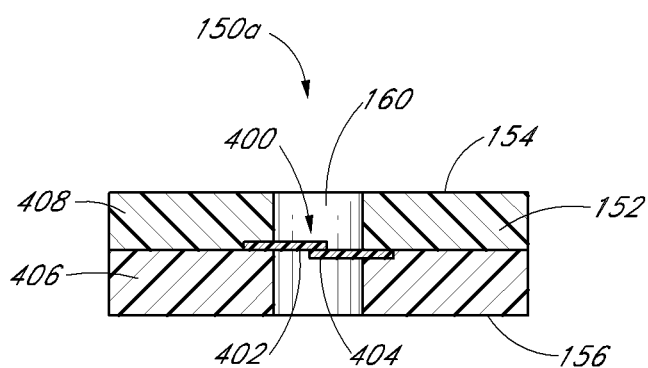
FIG. 27 is a cross-sectional view taken along line 27-27 of FIG. 26.

With reference next to FIGS. 26 and 27, another embodiment of a blocking member 150a is presented. In this embodiment, the blocking member 150a is shaped as a ring having an outer perimeter surface 158 and an inner aperture 160, and is configured to slidably fit about the catheter 232. However, the blocking member 150a comprises an inner aperture closure device 400 adapted to generally close the inner aperture 160 when the catheter 232 is removed therefrom. In the illustrated embodiment the closure device 400 comprises a pair of flexible flaps 402, 404 that are adapted to bend out of the way to accommodate the catheter 232, but which are biased to return to their places, preferably partially overlapping one another, when the catheter 232 is removed.

As best illustrated in FIG. 27, in the illustrated embodiment, the flexible flaps 402, 404 are incorporated into the body 152 of the blocking member 150*a*. For example, in one embodiment, a lower portion 406 of the blocking member 150*a* initially is manufactured separately; the flaps 402, 404 are fit in place on the lower portion 406; and then an upper portion 408 of the blocking member 150*a* is formed atop the lower portion 406 and portions of the flaps 402, 404. As such, the flaps 402, 404 are held securely as part of the blocking member 150*a*, but portions of the flaps 402, 404 extend transversely across the inner aperture 160. In another embodiment, the flaps 402, 404 may be adhered to a proximal or distal surface 154, 156 of the blocking member 150*a*.

Figure 28:
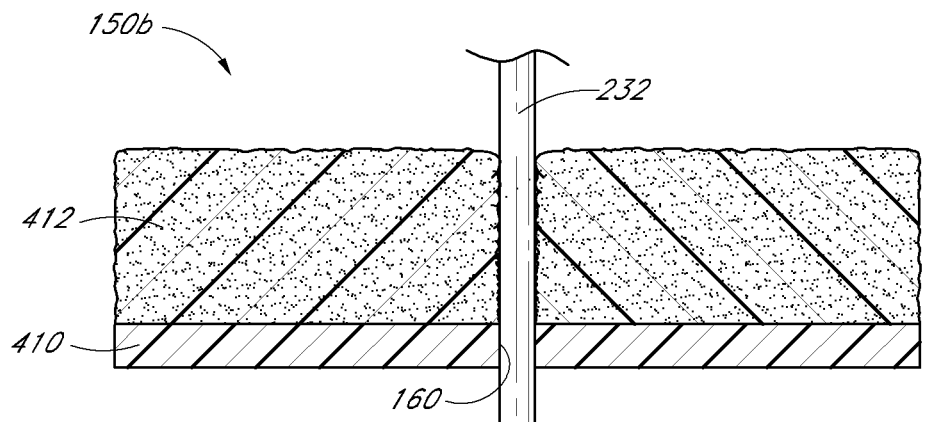
FIG. 28 is a sectional view of another embodiment of a blocking member having a catheter extending therethrough.
Figure 29:
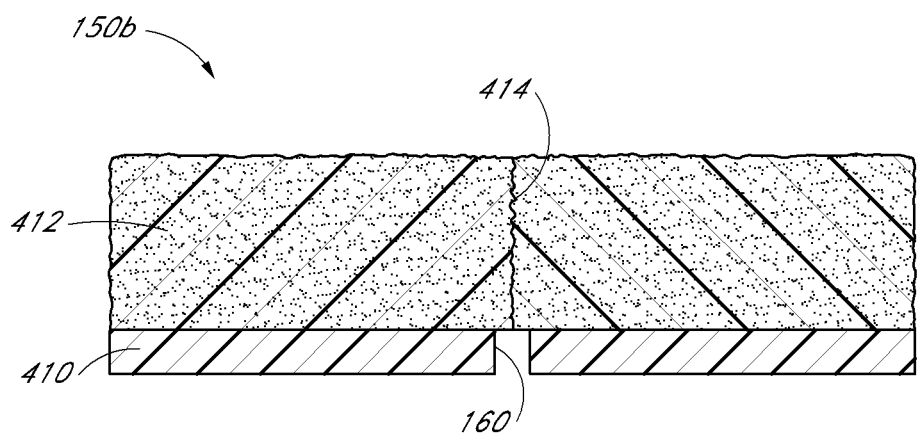
FIG. 29 shows the blocking member of FIG. 28 with the catheter removed.

With reference next to FIGS. 28 and 29, yet another embodiment of a blocking member 150*b* is presented in which the blocking member comprises multiple materials. In the illustrated embodiment, a body 152 of the blocking member 150*b* comprises a lower portion 410 and an upper portion 412. The lower portion 410 preferably is generally semirigid, is adapted to engage the blood vessel, and includes an inner aperture 160 sized and adapted to accommodate a locator catheter 232. The upper portion 412 preferably is generally elastic.

In a preferred embodiment, the upper portion 412 comprises an elastomeric foam that is deformable, but is adapted to return to its original shape once a deforming force is removed. Preferably, the upper portion 412 comprises a puncture 414, cut or the like that is generally aligned with the lower portion 410 inner aperture 160. The puncture 414 provides a path for a catheter 232 to extend through the upper portion 412 and through the lower portion 410 inner aperture 160. Portions of the upper portion 412 at and adjacent the puncture 414 are deformed (compacted) to accommodate the catheter 232, as shown specifically in FIG. 28. When the catheter 232 is removed, as shown specifically in FIG. 29, the compacted portions preferably return to their original shape, preferably plugging the puncture 414, and providing yet another barrier to prevent hemostatic material from passing through the inner aperture 160 and reaching the wound w.

Blocking members having closure media adapted to or biased so as to close the inner aperture upon removal of the catheter are particularly suited for use with hemostatic materials, such as dry powders, that may be particularly difficult to prevent from passing through small openings.

With reference next to FIGS. 30-32, yet another embodiment is presented illustrating an embodiment of a blocking member 150*c* and a corresponding pusher member 420. As shown, the blocking member 150*c* preferably comprises a body 152 having a distal surface 156, a proximal surface 154, and a perimeter surface 158. An inner aperture 160 is sized and adapted to accommodate an elongate catheter therethrough. A plurality of elongate arms 422 extend proximally from the proximal surface 154.

The pusher member 420 preferably comprises an elongate body 424 having a distal end 426 having a distal surface 428. A plurality of elongate tracks 430 extend proximally from the distal surface 428 and terminate at respective terminal walls 432. Preferably the tracks 430 are shaped generally complementarily to the arms 422 so that the arms 422 are slidably accommodated in the tracks 430. With particular reference to FIG. 31, preferably a space 434 is defined between the blocking member proximal surface 154 and the pusher member distal surface 428. Hemostatic material 333 preferably is disposed in the space 434.

With particular reference to FIGS. 31 and 32, preferably a length of the pusher tracks 430 is less than a length of the blocking member arms 422. As such, when proximal ends 436 of the arms 422 abut the terminal walls 432 of the track 430 as shown in FIG. 32, the space 434 between the pusher 420 and blocking member body 152 is preserved.

In use, preferably the blocking member 150*c* and pusher member 420 are initially engaged with one another with a hemostatic material 333 disposed in the space 434. As shown in FIG. 31, preferably the blocking member arms 422 are arranged in the tracks 430, but are spaced from the terminal walls 432. Preferably a catheter (not shown) extends through the pusher 420 and blocking member 150*c*, which are part of a vascular assembly. When the vascular assembly is positioned adjacent a vascular wound, the pusher 420 is moved distally to deploy the blocking member 150*c* and hemostatic material 333. As the blocking member 150*c* engages the wound, there is significant resistance to further distal progression. Eventually the pusher 420 moves distally relative the blocking member 150*c*, thus compressing the hemostatic material 333. Such relative movement is arrested when the arms 422 engage the track terminal walls 432. As such, excessive compression of the hemostatic material 333 by the pusher member 420 upon delivery is avoided.

There are many types of procedures that involve advancing a catheter and/or other surgical implement through a blood vessel puncture to perform therapy, deliver a device, or the like. The most common catheters used for interventions through the femoral artery are sized about 6 F or less. However, it is contemplated that much larger catheters and other surgical implements may be used. Closure apparatus as discussed herein may be constructed in many different sizes, as desired. Preferably the closure apparatus catheter 232 has a greater diameter than the catheter(s) and/or other surgical implements used in the procedure prior to closure. Preferably, the catheter 232 has a diameter about 0-1 F, and more preferably about 0.5 F, greater than earlier-used catheters. In the embodiment illustrated in FIGS. 12-25, the catheter 232 preferably is about 6.5 F in size.

Since the catheter 232 of the closure device is of greater diameter than the catheters used by the clinician prior to closure of the wound, the catheter 232 is large enough to tightly engage the wound edges and effectively plug the wound. This tight fit of the catheter 232 relative to the wound w further helps prevent hemostatic material 333 from passing between the catheter and wound edges and into the blood vessel 94.

As discussed above, a preferred embodiment blocking member has an outer diameter greater than the outer diameter of both the wound and the closure device catheter. The degree to which the blocking member outer diameter is greater than the wound diameter can vary, but preferably is chosen to eliminate a risk that the blocking member could pass through the wound when subjected to pressure from, for example, a pusher member. In a preferred embodiment, the blocking member has an outer diameter about 2-6 F, and more preferably about 3-4 F, greater than the wound, or than the largest device that entered the wound during the clinical procedure.

A closure device having aspects as discussed in the embodiments herein is especially relevant in connection with closing very large vascular punctures. For example, an ever-increasing number of procedures involve delivering relatively large treatment devices and/or prosthetics (such as heart valves or vascular grafts) through a vascular puncture. Such procedures may create a large puncture, such as a 10 F, 15 F or even 20 F puncture. For closing the puncture wound after such procedures, a blocking member having at least generally semi-rigid construction is especially helpful in that the entire wound may be covered by the blocking member to prevent other closure media from entering the wound. The blocking member may be supported by portions of the vessel unaffected by the puncture, and in turn the blocking member will support the punctured portion of the vessel. As such, the blocking member not only helps close the wound, but helps support the possibly-weakened portion of the vessel during healing.

In accordance with still another embodiment, a delivery tube 290 as in the embodiments described in connection with FIGS. 12-25 comprises indicia printed or otherwise marked thereon. In use, the clinician notes, during initial vascular puncture, the depth of the puncture. Later, during vessel closure, the indicia on the delivery tube 290 serves as a reference for the clinician to verify the depth of the tube and its position relative to the vascular wound. It is to be understood that such indicia may be printed on the delivery tube or may be physically formed as raised or lowered portions of the tube.

In another embodiment, indicia may be provided on a pusher member. Such indicia may be placed so as to help the user determine the position of the pusher member relative to the delivery tube, catheter and/or patient's skin in order to help determine whether the hemostatic material and blocking member have been fully deployed.

Figure 34:
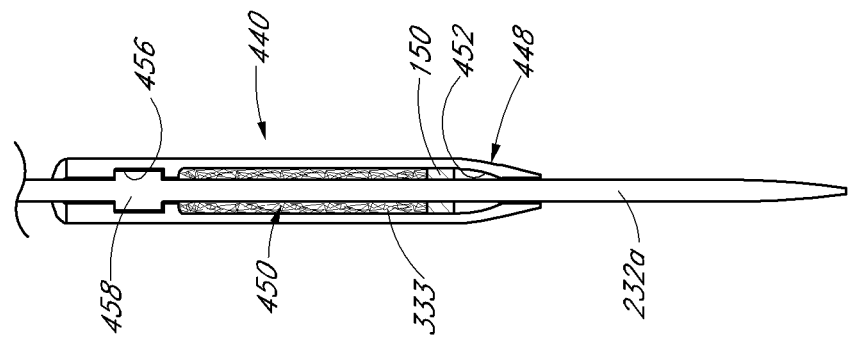
FIG. 34 shows an embodiment of a catheter disposed in the retractor arm of FIG. 33.

It is to be understood that delivery tubes of various shapes and sizes may be employed. For example, with reference next to FIGS. 33 and 34, another embodiment of a vascular closure device comprises a retractor comprising a pair of opposing elongate retractor arms 440. Preferably the retractor is configured to selectively open and close the retractor arms 440 when operated by a clinician. Each retractor arm 440 has a distal end 442 and a proximal end 444. Channels 446, 447 are formed at and immediately adjacent the distal and proximal ends 442, 444, and are configured to generally complementarily accommodate a catheter 232a, as shown in FIG. 34. Preferably a tapering portion 448 of the retractor arm 440 tapers to expand in outer diameter moving proximally from the distal end 442.

Each retractor arm 440 is at least partially hollow and a chamber 450 is defined between the retractor arms 440 when engaged with one another. After an initial taper 452, the chamber 450 preferably has a generally constant inner diameter. As shown specifically in FIG. 34, preferably the chamber 450 is adapted to accommodate a catheter 232a having a blocking member 150 disposed thereon, and a hemostatic material 333 arranged in the chamber 450 proximal the blocking member 150. In the illustrated embodiment, the chamber 450 initial taper 452 is generally sharp so that the blocking member 150 is arranged relatively close to the distal ends 442 of the retractor arms 440.

Figure 33:
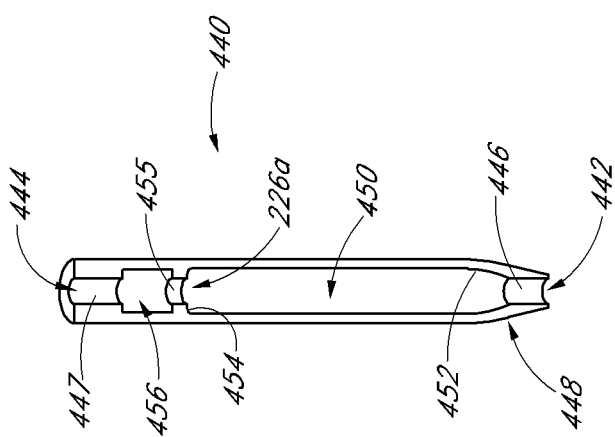
FIG. 33 shows a side plan view of one retractor arm of a retractor configured in accordance with one embodiment.

With continued reference to FIGS. 33 and 34, a proximal chamber wall 454 is defined at a proximal end 442 of the chamber 450. However, a channel 455 is provided to accommodate the catheter 232a extending therethrough. Proximal of the proximal chamber wall 454, a cavity 456 is formed within each retractor arm 440. Preferably, the catheter 232a comprises a raised portion 458 that is configured to fit complementarily into the cavity 456. As such, when the retractor arms 440 are engaged with the catheter 232a fit therein so that the catheter raised portion 458 is fit into the cavity 456, the catheter 232a is secured longitudinally relative to the retractor arms 440, and the assembly may be moved as a unit without concern that the position of the catheter (and thus the blocking ring) within the chamber 450 may be disturbed.

Figure 12:
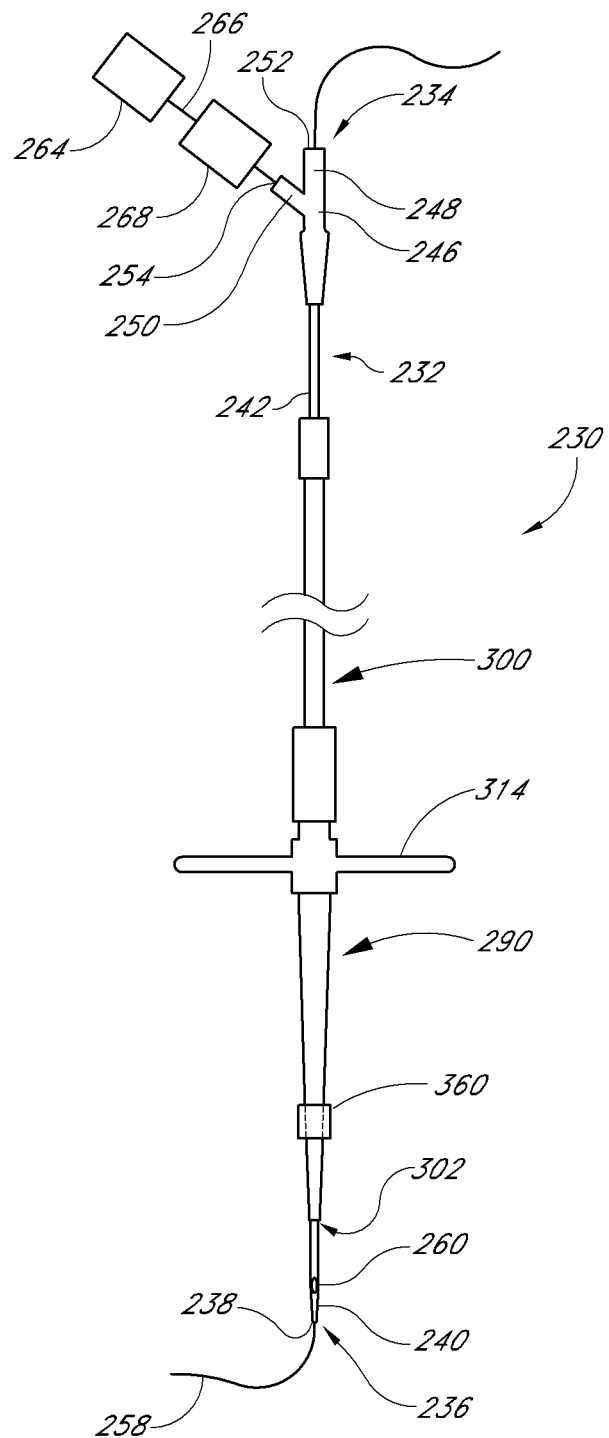
FIG. 12 is a side view of another embodiment of a vascular wound closure apparatus.

In accordance with a further embodiment, a delivery tube may be constructed that appears similar to the assembled tube illustrated in FIGS. 12 and 13, except that the tube is formed as a single piece rather than movable halves. In one embodiment, the one-piece tube comprises one or more longitudinally elongate weakened portions. In use, when force is applied to advance the pusher member, force is directed onto inner surfaces of the delivery tube chamber by the pusher member and/or the blocking member. Such forces break the weakened portions, thus opening a path for delivery of the blocking member and hemostatic material. In one embodiment, a pair of opposing elongate weakened portions are provided. In another embodiment, three or more such portions are provided. In still another embodiment, weakened portions are provided only in a distal portion of the delivery tube. In a still further embodiment, weakened portions extend the entire length of the delivery tube.

Figure 35:
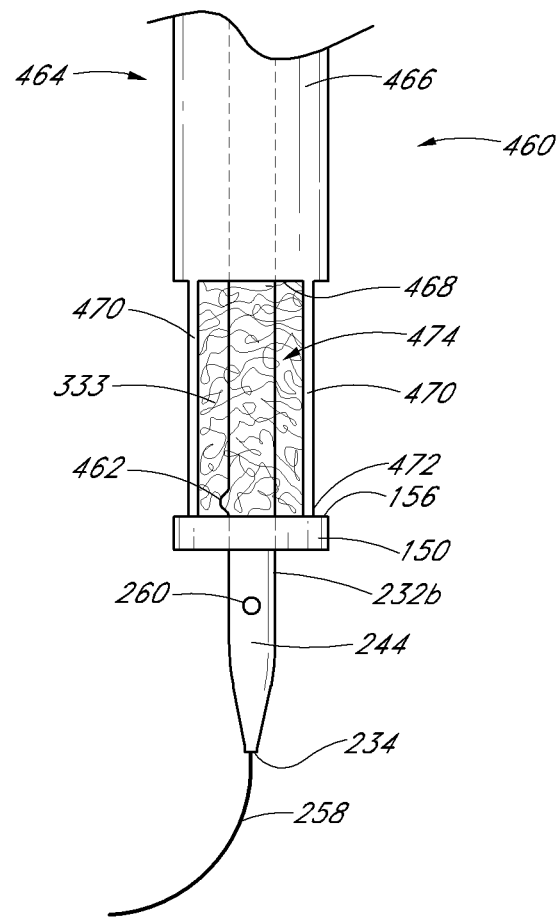
FIG. 35 shows yet another embodiment of a portion of a vascular wound closure device.

With reference next to FIG. 35, yet another embodiment of a vascular wound closure device 460 comprises a catheter 232b having a lumen 244 adapted to slidably accommodate a guidewire 258. Preferably the catheter 232b comprises an indicator hole 260 formed through a side wall of the catheter 232b proximal of a distal tip 234 of the catheter. A blocking member 150 is slidably arranged over the catheter 232b. As shown, the catheter preferably comprises a raised stop 462 along its length. Preferably the raised stop 462 protrudes enough to prevent the blocking member 150 from moving proximally along the catheter 232b past the stop 462. In one embodiment, the stop 462 prevents unwanted relative movement as the device 460 is advanced over the guidewire 258. In another embodiment, the stop 462 can help maintain a desired position of the blocking member 150 relative the catheter 232b when the catheter and blocking member 150 are loaded into a delivery tube, retractor chamber or the like.

A pusher member 464 is adapted to slide over the catheter 232b. The pusher member 464 comprises an elongate body 466 having a distal pushing surface 468. A plurality of elongate pusher arms 470 extend distally from the pusher surface 468. In the embodiment illustrated in FIG. 35, distal ends 472 of the pusher arms 470 engage the proximal surface 154 of the blocking member 150. As such, a minimum space 474 is defined between the pushing surface 468 and the blocking member 150. In the illustrated embodiment, the space 474 is filled with a hemostatic material 333. In one embodiment, the arms 470 engage and can advance the blocking member 150 towards the wound independent of the hemostatic material 333; the pushing surface 468 engages the hemostatic material 333 and advances it toward the wound independent of the blocking member 150.

In use, the apparatus is advanced over the guidewire 258 while a vacuum is being drawn through the catheter 232b until blood is drawn through the indicator hole 260, indicating that the blocking member 150 is disposed at or adjacent the vascular wound. The pusher member 464 is then advanced distally, thus advancing the blocking member 150 and hemostatic material 333 to the wound site without substantially compacting the hemostatic material 333. In another embodiment, a distal portion of the hemostatic material 333 is adhered to the proximal surface 156 of the blocking member 150. As such, during advancement, the blocking member 150 pulls the hemostatic material 333 after it as the pusher 464 advances the blocking member 150 toward the wound.

In another embodiment, the pusher arms 470 are spring-loaded relative to the pusher. As such, the space may be at least partially compressed as the pusher delivers the blocking member and hemostatic material to the wound site. In yet another embodiment, the distal ends of the pusher member arms are mildly bonded to the proximal surface of the blocking member. As such, the assembly is held together when the pusher member advances the blocking member and hemostatic material to the wound site. When appropriately delivered, a twist of the pusher member relative the blocking member breaks the mild bond, and the pusher may be removed.

Figure 36:
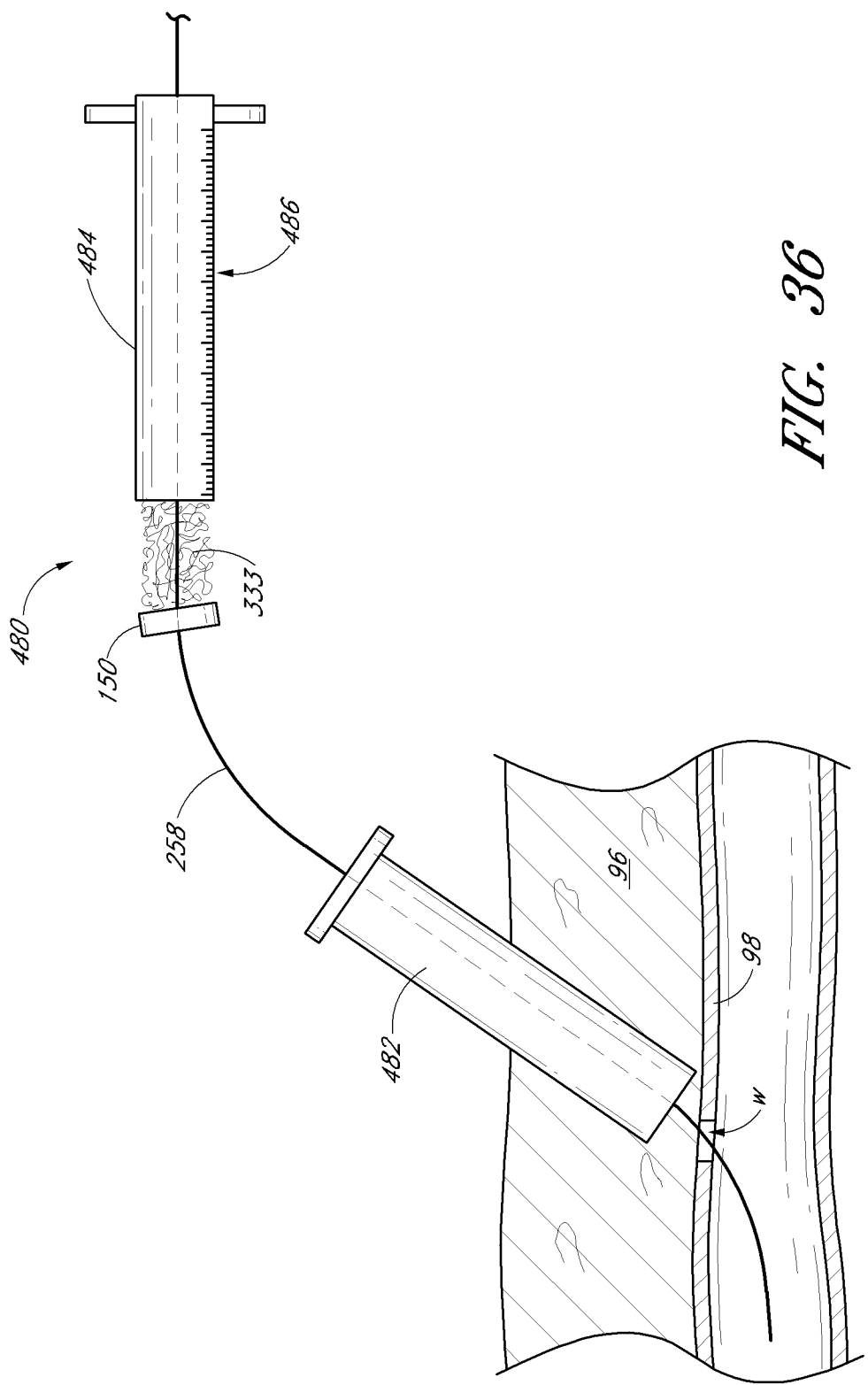
FIG. 36 illustrates yet another embodiment of a vascular wound closure assembly.
Figure 37:
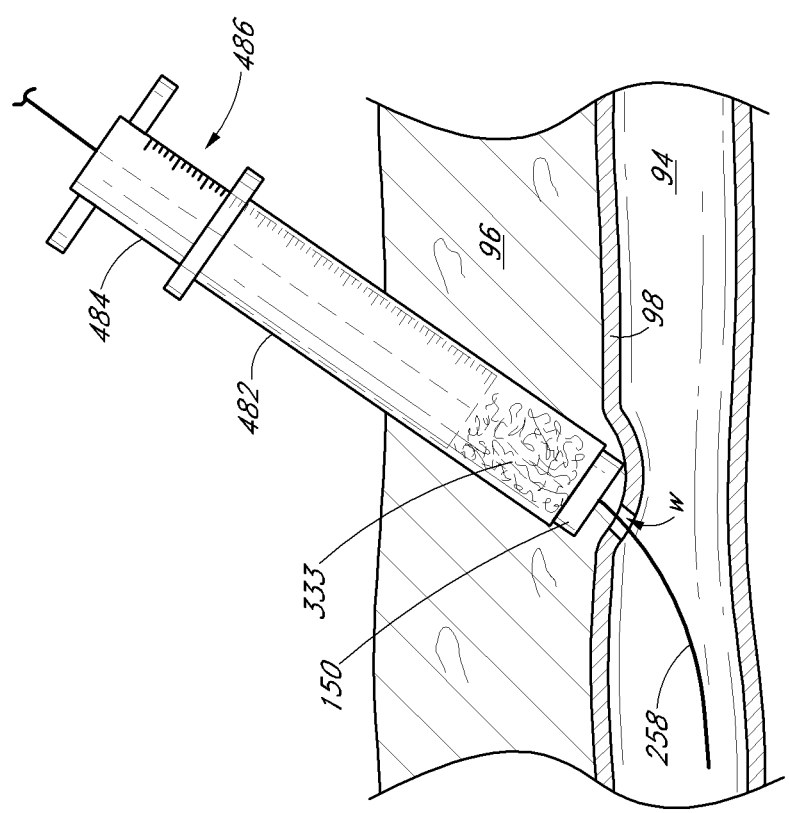
FIG. 37 illustrates the assembly of FIG. 36 advanced into position adjacent a blood vessel wall.

With reference next to FIGS. 36 and 37, another embodiment is provided in which a vascular wound closure assembly 480 is advanced over a guidewire 258, through an elongate sheath 482 and to a vascular wound w. In the illustrated embodiment, a path to a position at or adjacent the wound w is maintained by the sheath 482. The vascular wound closure assembly 480 comprises a blocking member 150 having an inner aperture 160 with an inner diameter sized and adapted to accommodate the guidewire 258. The illustrated embodiment does not employ a catheter, although it is contemplated that additional embodiments may employ a catheter. Hemostatic material 333 is arranged over the guidewire 258 proximal the blocking member 150. An elongate pusher member 484 is configured to advance the hemostatic material 333 and blocking member 150 distally over the guidewire 258, through the sheath 482, and into contact with the wound w as shown in FIG. 37.

In the illustrated embodiment, the pusher member 484 has indicia 486 printed on its side. The indicia 486 are calibrated relative to the length of the sheath 482, and thus can indicate the position of the pusher member 484 relative to the sheath 482. As such, the clinician can determine whether the blocking member 150 and hemostatic material 333 have been advanced distally enough to appropriately engage the blood vessel outer wall 98 so as to close the wound w.

Various methods may be used to put the sheath 482 in place. In one embodiment, a hollow needle is first inserted into the vessel, and the guidewire 258 is advanced through the needle and into the vessel 94, and the needle is withdrawn. An introducer sheath can be advanced over the guidewire 258, and may enter the vessel 94. An outer sheath of increased cross section can be advanced over the introducer sheath. However, due to its larger diameter, the outer sheath does not enter the vessel, although the introducer sheath functions as a path to introduce treatment media into the vessel 94 during the procedure. Preferably the outer sheath remains in place after the treatment procedure is completed and the introducer sheath is removed from the vessel. As such, the outer sheath 482 provides the path for the vessel wound closure assembly 480.

Figure 38:
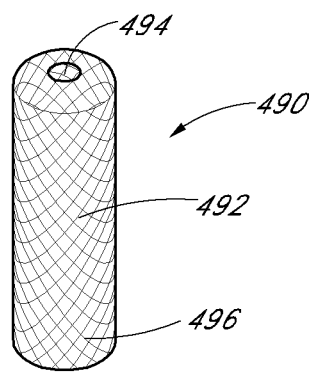
FIG. 38 is a perspective view of a sac adapted to contain hemostatic material in accordance with one embodiment.

With reference next to FIG. 38, a bag or sac 490 is disclosed. Preferably, the sac 490 comprises an elongate body 492 shaped generally as an elongate torus. As such, an elongate aperture 494 is formed through the sac 490. In a preferred embodiment, the sac 490 comprises a fibrous mesh material 496 and is adapted to enclose a hemostatic material therein. In another embodiment, the sac 490 comprises a material that readily degrades upon exposure to body tissues. For example, the sac 490 may be formed of a dried gelatinous material that, upon exposure to wet body tissues, including blood, absorbs water and melts, thus exposing the hemostatic material therewithin.

Figure 39:
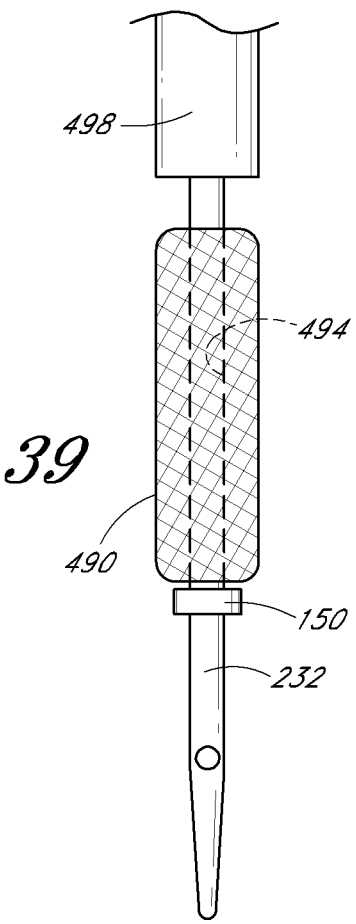
FIG. 39 shows the sac of FIG. 38 arranged on a catheter proximal a blocking member.
Figure 40:
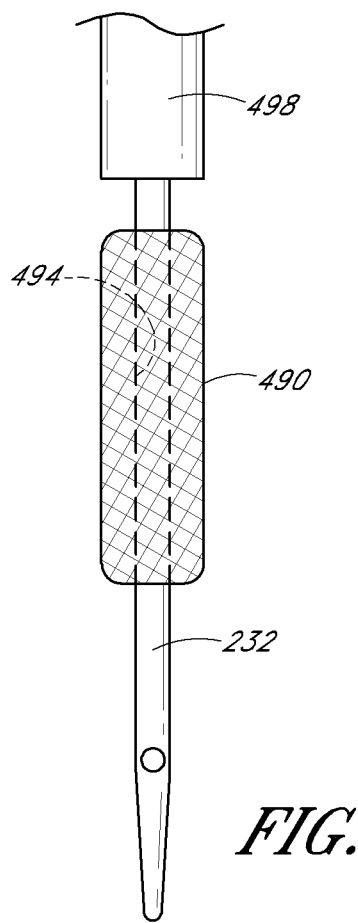
FIG. 40 shows the sac of FIG. 38 arranged on a catheter.

With reference also to FIG. 39, in one embodiment, the sac 490 may be arranged over a catheter 232 and proximal a blocking member 150. As such, the sac 490 can be used as modifications of embodiments discussed herein. A push member 498 is provided to advance the sac and blocking member 150 over the catheter 232. With reference to FIG. 40, in another embodiment, the sac 490 (such as a mesh sac) functions as its own blocking member arranged between the wound w and the hemostatic material within the sac. Due to the mesh structure, the hemostatic material is contained within the sac. However, blood can flow through the mesh 496 into the hemostatic material, prompting a coagulation cascade, which can also proceed through the mesh 496.

In another embodiment, rather than employing an enclosed mesh sac, the hemostatic material may be disposed in a mesh tray. The tray comprises a flexible, semi-rigid, or generally rigid mesh or screen material at its distal end and along sides, but is open at its proximal end.

In accordance with another embodiment, a vascular wound closure apparatus having features as in an embodiment discussed above is provided in a kit for use by a clinician. In this embodiment, the apparatus preferably is formed of a disposable, yet suitable material, such as a medical grade plastic, and is assembled and loaded so that the members are releasably coupled to one another and hemostatic material is disposed in the delivery tube. Although the apparatus may be provided pre-assembled, a clinician may still adjust the position of the tube relative to the catheter by decoupling the tube and pusher member, making the adjustment, and then recoupling the tube and pusher member. The apparatus is sterilized and preferably is disposed within a closed, sterilized container (not shown) which is configured to be opened in a sterile environment such as an operating room or catheter lab.

Although this disclosure has presented certain preferred embodiments and examples, it will be understood by those skilled in the art that the present inventions extend beyond the specifically disclosed embodiments to other alternative embodiments and/or uses and obvious modifications and equivalents thereof. In addition, while a number of variations have been shown and described in detail, other modifications, which are within the scope of invention, will be readily apparent to those of skill in the art based upon this disclosure. It is also contemplated that various combinations or subcombinations of the specific features and aspects of the embodiments may be made and still fall within the inventive scope. For example, a raised stop as discussed above in connection with the embodiment illustrated in FIG. 35 could suitably be combined with the embodiments discussed in connection with FIGS. 12-25. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

What is claimed is:

1. A vascular wound closure device, comprising:
an elongate catheter sized and configured to extend partially through a vascular puncture;
an elongate delivery tube disposed about the catheter so that the catheter extends through the delivery tube and a distal end of the delivery tube approximates the catheter, an inner surface of the delivery tube proximal of the distal end being spaced from the catheter so as to define a delivery tube chamber between the catheter and the delivery tube, the delivery tube chamber tapering so that a diameter of the delivery tube chamber decreases moving distally along at least a portion of a length of the chamber;

a multi-layer closure portion disposed circumferentially about the elongate catheter, the closure portion being movable distally over the elongate catheter;
  a first member of the closure portion configured to engage a blood vessel wall and having an outer diameter that is greater than a diameter of the vascular puncture, the first member comprising an aperture having an aperture diameter and an aperture surface;
  a second member of the closure portion comprising a hemostatic material; and
a push member that is movable longitudinally over the catheter, the push member configured to engage and apply an advancement force to at least one of the first and second members so as to move the first and second members distally over the catheter;
wherein the closure portion is disposed within the delivery tube chamber at a staging position at which the outer diameter of the first member is substantially the same as the diameter of the tapering delivery tube chamber so that the first member is spaced proximally from a distal end of the delivery tube chamber; and
wherein at least part of the first member is arranged distal of the second member, and the elongate catheter extends through the first member aperture so that the aperture surface of the first member engages an outer surface of the elongate catheter, the first member aperture diameter being sized and configured so that the aperture surface slidably engages the outer surface of the elongate catheter sufficient to create a seal between the aperture surface and the catheter outer surface so that the hemostatic material of the second member is prevented from moving distally between the first member and the outer surface of the catheter.

2. A vascular wound closure device as in claim 1, wherein the first member is movable separately from the second member.

3. A vascular wound closure device as in claim 1, wherein the second member is adhered to the first member.

4. A vascular wound closure device as in claim 1, wherein the delivery tube comprises a retractor.

5. A vascular wound closure device as in claim 1, wherein the catheter is movable over a guidewire.

6. A vascular wound closure device as in claim 1, wherein the push member is arranged about the catheter, and the push member is adapted to engage the first member so that a space is defined between a distal surface of the push member and a proximal surface of the first member.

7. A vascular wound closure device as in claim 1, wherein the first member comprises a hemostatic material.

8. A vascular wound closure device as in claim 7, wherein the first member is generally rigid.

9. A vascular wound closure device as in claim 7, wherein the first member comprises chitosan.

10. A vascular wound closure device as in claim 9, wherein the second member comprises a fibrous chitosan fleece.

11. A vascular wound closure device as in claim 10, wherein the first member has a greater density than the second member.

12. A vascular wound closure device as in claim 1, wherein the first member and the delivery tube are sized and configured so that a circumferential surface of the first member engages the inner surface of the delivery tube sufficient to create a seal preventing material from the second member from moving distally between the first member and the delivery tube inner surface.

13. A vascular wound closure device as in claim 1, wherein the delivery tube comprises a plurality of tube members that selectively engage one another to form the delivery tube when engaged, and an outer surface of the delivery tube is generally tapered toward the distal end.

14. A vascular wound closure device as in claim 13 additionally comprising an expandable collar movably disposed on the delivery tube outer surface, the expandable collar adapted to exert an inwardly-directed force tending to urge the tube members to remain engaged.

15. A vascular wound closure device as in claim 14, wherein the expandable collar has a collar staging position wherein the collar is disposed on the delivery tube outer surface directly opposite the staging position of the first member of the closure portion inside the delivery tube chamber.

16. A vascular wound closure device as in claim 15, wherein when the first member of the closure portion is at the staging position, a circumferential surface of the first member engages the inner surface of the delivery tube sufficient to create a seal between the circumferential surface and the inner surface so that the hemostatic material of the second member is prevented from moving distally between the first member and the inner surface of the delivery tube.

17. A vascular wound closure device as in claim 16, wherein the collar staging position is on a tapered portion of the delivery tube outer surface.

* * * * *

UNITED STATES PATENT AND TRADEMARK OFFICE
CERTIFICATE OF CORRECTION

PATENT NO. : 8,617,253 B2
APPLICATION NO. : 13/308922
DATED : December 31, 2013
INVENTOR(S) : Zhu et al.

Page 1 of 1

It is certified that error appears in the above-identified patent and that said Letters Patent is hereby corrected as shown below:

On the Title Page

Column 2 (page 3, item [56]) at line 5, Under "Other Publications" change "Hemospheres" to --Hemispheres--.

Column 2 (page 3, item [56]) at line 7, Under "Other Publications" change "MEDAFORE" to --MEDAFOR--.

In the Specification

Column 4 at line 6, Change "12" to --12.--.

Column 5 at line 1, Change "OF" to --OF THE--.

Column 17 at line 10, Change "Mock" to --J-lock--.

Column 20 at lines 29-30, Change "hydrophillic" to --hydrophilic--.

Signed and Sealed this
Fifteenth Day of July, 2014

Michelle K. Lee
*Deputy Director of the United States Patent and Trademark Office*